(12) United States Patent
Michiyuki

(10) Patent No.: US 11,512,343 B2
(45) Date of Patent: Nov. 29, 2022

(54) OLIGONUCLEOTIDE PROBE FOR DETECTING SINGLE NUCLEOTIDE POLYMORPHISM, AND METHOD FOR DETECTING SINGLE NUCLEOTIDE POLYMORPHISM

(71) Applicant: Eiken Kagaku Kabushiki Kaisha, Tokyo (JP)

(72) Inventor: Satoru Michiyuki, Tochigi (JP)

(73) Assignee: Eiken Kagaku Kabushiki Kaisha, Tokyo (JP)

( * ) Notice: Subject to any disclaimer, the term of this patent is extended or adjusted under 35 U.S.C. 154(b) by 645 days.

(21) Appl. No.: 15/537,121

(22) PCT Filed: Dec. 2, 2015

(86) PCT No.: PCT/JP2015/083899
§ 371 (c)(1),
(2) Date: Jun. 16, 2017

(87) PCT Pub. No.: WO2016/098595
PCT Pub. Date: Jun. 23, 2016

(65) Prior Publication Data
US 2017/0342471 A1 Nov. 30, 2017

(30) Foreign Application Priority Data
Dec. 19, 2014 (JP) .............................. JP2014-257198

(51) Int. Cl.
| | | |
|---|---|---|
| C07H 21/04 | (2006.01) |
| C07H 21/00 | (2006.01) |
| G01N 33/00 | (2006.01) |
| C12Q 1/6827 | (2018.01) |
| C12N 15/09 | (2006.01) |
| C12Q 1/68 | (2018.01) |
| C12Q 1/6825 | (2018.01) |

(52) U.S. Cl.
CPC .......... *C12Q 1/6827* (2013.01); *C12N 15/09* (2013.01); *C12Q 1/68* (2013.01); *C12Q 1/6825* (2013.01)

(58) Field of Classification Search
None
See application file for complete search history.

(56) References Cited

U.S. PATENT DOCUMENTS

| | | | | |
|---|---|---|---|---|
| 6,444,661 B1 * | 9/2002 | Barton .................. | C07F 15/008 |
| | | | 514/185 |
| 9,315,857 B2 * | 4/2016 | Fu ........................ | C12Q 1/6837 |
| 2001/0000175 A1 | 4/2001 | Kurane et al. | |
| 2005/0042638 A1 | 2/2005 | Arnold, Jr. et al. | |
| 2006/0281099 A1 | 12/2006 | Breneman et al. | |
| 2006/0286570 A1 * | 12/2006 | Rowlen .................. | C12Q 1/6816 |
| | | | 435/6.12 |
| 2007/0009954 A1 * | 1/2007 | Wang .................... | C12Q 1/6823 |
| | | | 435/6.12 |
| 2007/0031829 A1 * | 2/2007 | Yasuno ................ | C12Q 1/6886 |
| | | | 435/6.12 |
| 2007/0042419 A1 * | 2/2007 | Barany ................ | C12Q 1/6813 |
| | | | 435/6.12 |
| 2009/0176231 A1 * | 7/2009 | Hirai .................... | C12Q 1/6886 |
| | | | 435/6.16 |
| 2011/0039264 A1 | 2/2011 | Will | |
| 2012/0165219 A1 * | 6/2012 | Van ..................... | C12Q 1/6834 |
| | | | 506/9 |
| 2012/0220468 A1 * | 8/2012 | Chun .................... | C07H 21/00 |
| | | | 506/4 |
| 2013/0295570 A1 * | 11/2013 | Wangh ................. | C12Q 1/6827 |
| | | | 435/6.11 |
| 2014/0193815 A1 | 7/2014 | Arnold, Jr. et al. | |
| 2014/0227683 A1 * | 8/2014 | Cobb ................... | C12Q 1/6818 |
| | | | 435/5 |

FOREIGN PATENT DOCUMENTS

| | | |
|---|---|---|
| CN | 101074450 A | 11/2007 |
| CN | 102471805 A | 5/2012 |
| CN | 103998624 A | 8/2014 |
| EP | 2523965 A1 | 11/2012 |
| JP | 2001-286300 A | 10/2001 |
| JP | 2006-525027 A | 11/2006 |
| JP | 2013-501508 A | 1/2013 |

(Continued)

OTHER PUBLICATIONS

"Oligonucleotide definition," Merriam-Webster.com; accessed Aug. 23, 2017. (Year: 2017).*
"Archaea," Wikipedia.com, accessed May 11, 2016. (Year: 2016).*
"Viruses", Wikipedia.com, accessed Nov. 24, 2012. (Year: 2012).*
"How many species of bacteria are there", wisegeek.com; accessed Jan. 21, 2014. (Year: 2014).*
"Fungi," Wikipedia.com; accessed Jun. 3, 2013. (Year: 2013).*
"Plant," Wikipedia.com; accessed Aug. 28, 2015. (Year: 2015).*
"Mammal," Wikipedia.com, accessed Sep. 22, 2011. (Year: 2011).*
"Murinae," Wikipedia.com, accessed Mar. 18, 2013. (Year: 2013).*
"Fish," Wikipedia.com, accessed Nov. 2, 2014. (Year: 2014).*
"Algae," Wikipedia.com, accessed Mar. 4, 2016. (Year: 2016).*

(Continued)

*Primary Examiner* — Bradley L. Sisson
(74) *Attorney, Agent, or Firm* — Morgan, Lewis & Bockius LLP

(57) ABSTRACT

The present invention provides an oligonucleotide probe for single nucleotide polymorphism detection to be used for a target nucleic acid where a single nucleotide polymorphism is present, the oligonucleotide probe comprising a reporter region, an anchor region, and a linker region. The reporter region comprises: an oligonucleotide consisting of a sequence perfectly matching when a nucleotide of the single nucleotide polymorphism is a first nucleotide, and mismatching when the nucleotide of the single nucleotide polymorphism is a nucleotide other than the first nucleotide; and a fluorescent dye quenching when the reporter region hybridize to the target nucleic acid.

13 Claims, 10 Drawing Sheets
Specification includes a Sequence Listing.

(56) References Cited

FOREIGN PATENT DOCUMENTS

| JP | 2014-526257 A | 10/2014 |
|---|---|---|
| WO | 02/050308 A1 | 6/2002 |
| WO | 2004/000995 A2 | 12/2003 |
| WO | 2004/098386 A2 | 11/2004 |
| WO | 2007/018734 A2 | 2/2007 |
| WO | 2011/018232 A1 | 2/2011 |
| WO | 2011/087928 A1 | 7/2011 |
| WO | 2013/041853 A1 | 3/2013 |

OTHER PUBLICATIONS

"Protozoa," Wikipedia.com, accessed May 11, 2016. (Year: 2016).*
"List of sequenced bacterial genomes", Wikipedia.com; accessed Jan. 24, 2014. (Year: 2014).*
Forster et al., "A human gut bacterial genome and culture collection for improved metagenomic analyses", Nature Biotechnology, vol. 37, Feb. 2019, 186-192. (Year: 2019).*
Teixeira and Cooper, "Using hominin introgression to trace modern human dispersals", PNAS, vol. 116, No. 31, Jul. 30, 2019, pp. 15327-15332. (Year: 2019).*
Zhang et al., "Reconstruction of DNA sequencing by hybridization", Bioinformatics, vol. 19, No. 1, 2003, pp. 14-21. (Year: 2003).*
Nobori et al., "Advances in genetic diagnosis: Its accomplishment and the prospects for the future," Clinical Testing, 56:515-520 (2012).
International Search Report issued in corresponding International Patent Application No. PCT/JP2015/083899 dated Feb. 23, 2016.
International Preliminary Report on Patentability and Written Opinion issued in corresponding International Patent Application No. PCT/JP2015/083899 dated Jun. 29, 2017.
Faltin et al., "Current Methods for Fluorescence-Based Universal Sequence-Dependent Detection of Nucleic Acids in Homogenous Assays and Clinical Applications," Clinical Chemistry, 59:1567-1582 (2013).
Tani et al., "Universal Quenching Probe System: Flexible, Specific, and Cost-Effective Real-Time Polymerase Chain Reaction Method," Analytical Chemistry, 81: 5678-5685 (2009).
Nazarenko et al., "Effect of primary and secondary structure of oligodeoxyribonucleotides on the fluorescent properties of conjugated dyes," Nucleic Acids Research, 30: 2089-2195 (2002).
Rimour et al., "GoArrays: highly dynamic and efficient microarray probe design," Bioinformatics, 21: 1094-1103 (2005).
Suzuki et al., "Development of a Novel, Fully-Automated Genotyping System: Principle and Applications," Sensors, 12: 16614-16627 (2012).
Extended European Search Report issued in counterpart European Patent Application No. 15869801.9 dated Jul. 5, 2018.
Office Action issued in counterpart European Patent Application No. 15869801.9 dated Jul. 31, 2019.

* cited by examiner

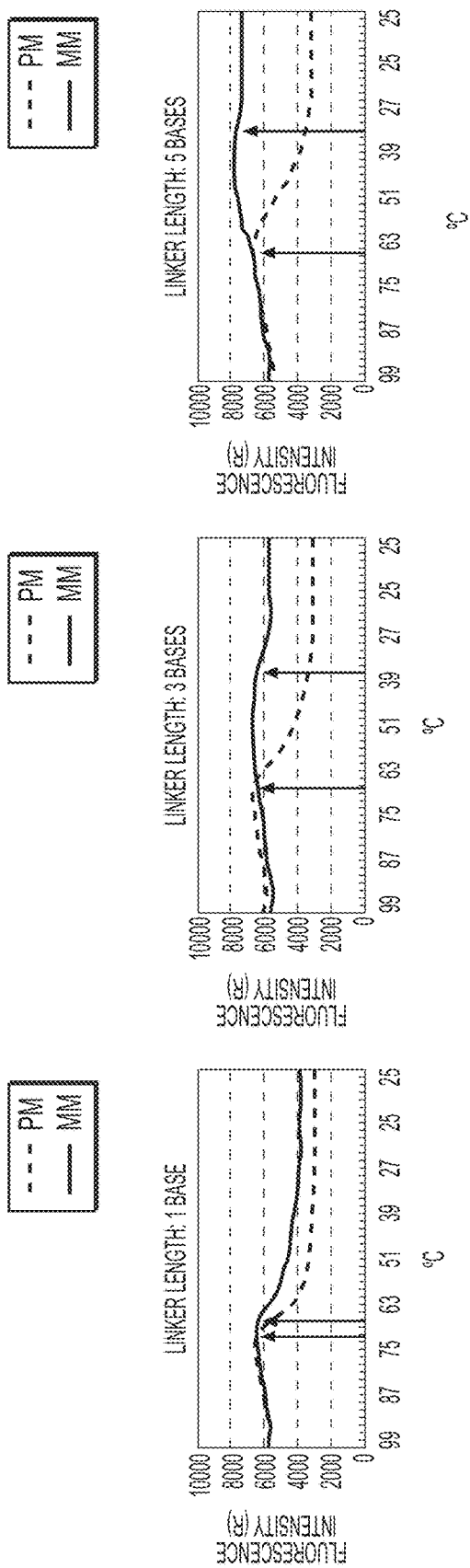
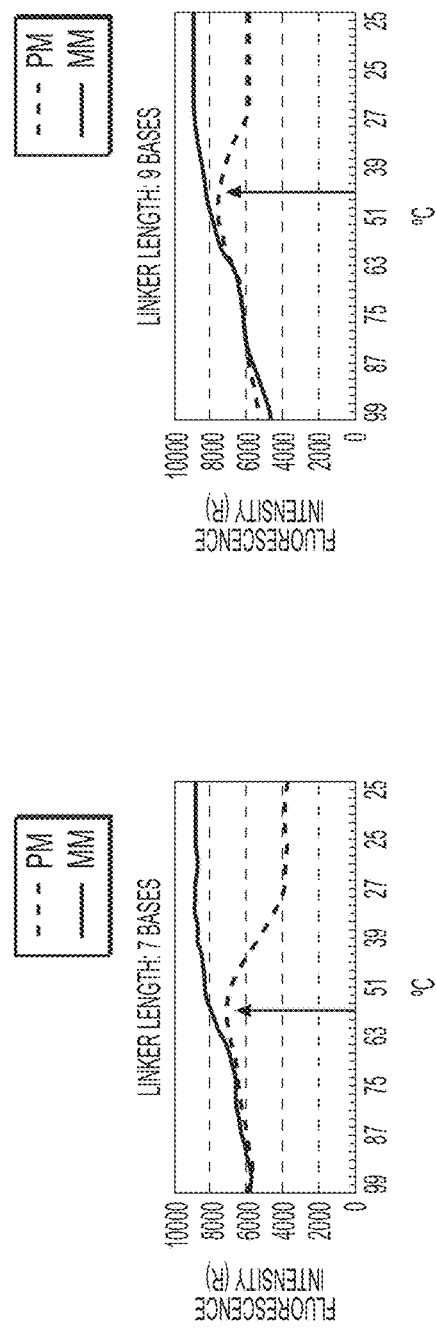
FIG. 3A  FIG. 3B  FIG. 3C  FIG. 3D  FIG. 3E

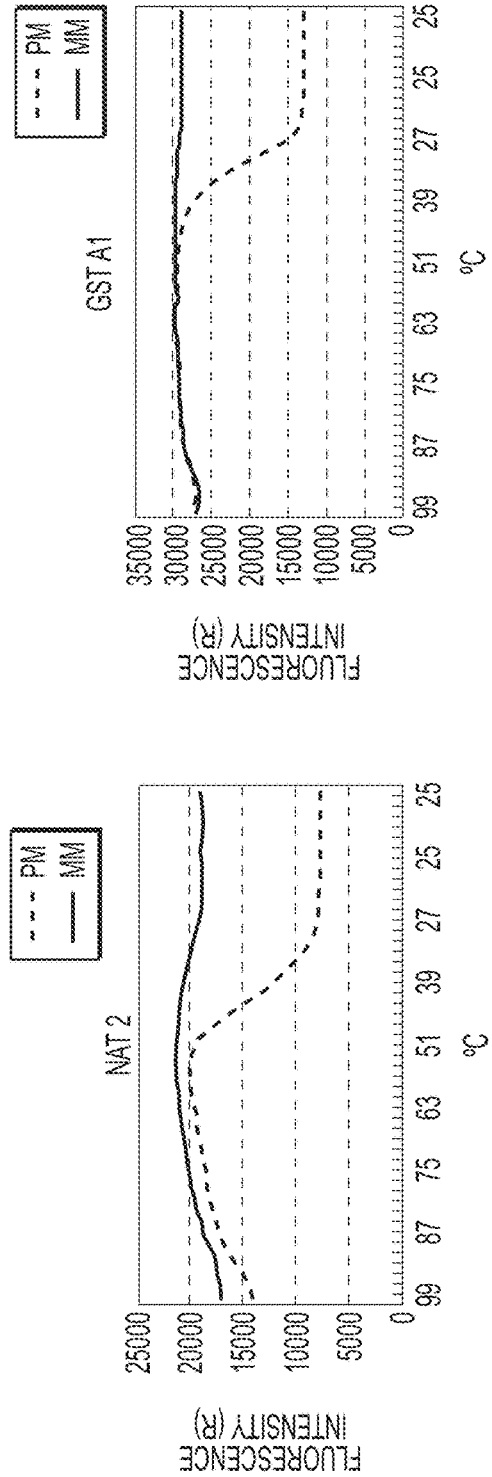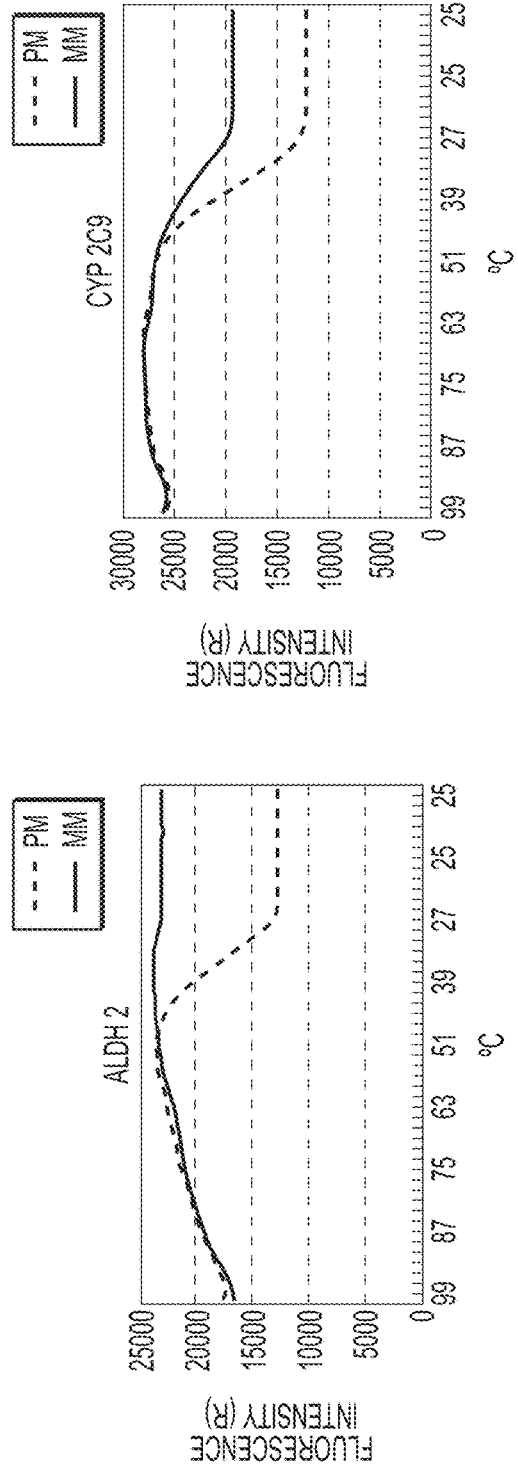
FIG. 5A  FIG. 5B  FIG. 5C  FIG. 5D

SEQUENCE LISTING

```
<160> NUMBER OF SEQ ID NOS: 44

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
acagcgggtt gttctggtc                                              19

<210> SEQ ID NO 2
<211> LENGTH: 6
<212> TYPE: DNA
<213> ORGANISM: Artificial Sequence
<220> FEATURE:
<223> OTHER INFORMATION: Synthetic

<400> SEQUENCE: 2 gaccag                                                             6

<210> SEQ ID NO 3
<211> LENGTH: 6
<212> TYPE: DNA
<213> ORGANISM: Artificial Sequence
<220> FEATURE:
<223> OTHER INFORMATION: Synthetic

<400> SEQUENCE: 3 gtccag                                                             6

<210> SEQ ID NO 4
<211> LENGTH: 7
<212> TYPE: DNA
<213> ORGANISM: Artificial Sequence
<220> FEATURE:
<223> OTHER INFORMATION: Synthetic

<400> SEQUENCE: 4 gaccaga                                                            7

<210> SEQ ID NO 5
<211> LENGTH: 7
<212> TYPE: DNA
<213> ORGANISM: Artificial Sequence
<220> FEATURE:
<223> OTHER INFORMATION: Synthetic

<400> SEQUENCE: 5 gtccaga                                                            7

<210> SEQ ID NO 6
<211> LENGTH: 8
<212> TYPE: DNA
<213> ORGANISM: Artificial Sequence
<220> FEATURE:
<223> OTHER INFORMATION: Synthetic
```

```
<400> SEQUENCE: 6 gaccagaa                                                             8

<210> SEQ ID NO 7
<211> LENGTH: 8
<212> TYPE: DNA
<213> ORGANISM: Artificial Sequence
<220> FEATURE:
<223> OTHER INFORMATION: Synthetic

<400> SEQUENCE: 7 gtccagaa                                                             8

<210> SEQ ID NO 8
<211> LENGTH: 9
<212> TYPE: DNA
<213> ORGANISM: Artificial Sequence
<220> FEATURE:
<223> OTHER INFORMATION: Synthetic

<400> SEQUENCE: 8 gaccagaac                                                            9

<210> SEQ ID NO 9
<211> LENGTH: 9
<212> TYPE: DNA
<213> ORGANISM: Artificial Sequence
<220> FEATURE:
<223> OTHER INFORMATION: Synthetic

<400> SEQUENCE: 9 gtccagaac                                                            9

<210> SEQ ID NO 10
<211> LENGTH: 10
<212> TYPE: DNA
<213> ORGANISM: Artificial Sequence
<220> FEATURE:
<223> OTHER INFORMATION: Synthetic

<400> SEQUENCE: 10
gaccagaaca                                                          10

<210> SEQ ID NO 11
<211> LENGTH: 10
<212> TYPE: DNA
<213> ORGANISM: Artificial Sequence
<220> FEATURE:
<223> OTHER INFORMATION: Synthetic

<400> SEQUENCE: 11
gtccagaaca                                                          10

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
gaccaagaac aacccgctgt                                               20

<210> SEQ ID NO 13
```

```
<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
gtccaagaac aacccgctgt                                                    20

<210> SEQ ID NO 14
<211> LENGTH: 22
<212> TYPE: DNA
<213> ORGANISM: Artificial Sequence
<220> FEATURE:
<223> OTHER INFORMATION: Synthetic

<400> SEQUENCE: 14
gaccaaaaga acaacccgct gt                                                 22

<210> SEQ ID NO 15
<211> LENGTH: 22
<212> TYPE: DNA
<213> ORGANISM: Artificial Sequence
<220> FEATURE:
<223> OTHER INFORMATION: Synthetic

<400> SEQUENCE: 15
gtccaaaaga acaacccgct gt                                                 22

<210> SEQ ID NO 16
<211> LENGTH: 24
<212> TYPE: DNA
<213> ORGANISM: Artificial Sequence
<220> FEATURE:
<223> OTHER INFORMATION: Synthetic

<400> SEQUENCE: 16
gaccaaaaaa gaacaacccg ctgt                                               24

<210> SEQ ID NO 17
<211> LENGTH: 24
<212> TYPE: DNA
<213> ORGANISM: Artificial Sequence
<220> FEATURE:
<223> OTHER INFORMATION: Synthetic

<400> SEQUENCE: 17
gtccaaaaaa gaacaacccg ctgt                                               24

<210> SEQ ID NO 18
<211> LENGTH: 26
<212> TYPE: DNA
<213> ORGANISM: Artificial Sequence
<220> FEATURE:
<223> OTHER INFORMATION: Synthetic

<400> SEQUENCE: 18
gaccaaaaaa aagaacaacc cgctgt                                             26

<210> SEQ ID NO 19
<211> LENGTH: 26
<212> TYPE: DNA
<213> ORGANISM: Artificial Sequence
<220> FEATURE:
<223> OTHER INFORMATION: Synthetic

<400> SEQUENCE: 19
```
gtccaaaaaa aagaacaacc cgctgt                                            26

<210> SEQ ID NO 20
<211> LENGTH: 28
<212> TYPE: DNA
<213> ORGANISM: Artificial Sequence
<220> FEATURE:
<223> OTHER INFORMATION: Synthetic

<400> SEQUENCE: 20
gaccaaaaaa aaagaacaa cccgctgt                                           28

<210> SEQ ID NO 21
<211> LENGTH: 28
<212> TYPE: DNA
<213> ORGANISM: Artificial Sequence
<220> FEATURE:
<223> OTHER INFORMATION: Synthetic

<400> SEQUENCE: 21
gtccaaaaaa aaagaacaa cccgctgt                                           28

<210> SEQ ID NO 22
<211> LENGTH: 40
<212> TYPE: DNA
<213> ORGANISM: Artificial Sequence
<220> FEATURE:
<223> OTHER INFORMATION: Synthetic

<400> SEQUENCE: 22
cattgacctt ctccccacca gcctgcccca tgcagtgacc                             40

<210> SEQ ID NO 23
<211> LENGTH: 40
<212> TYPE: DNA
<213> ORGANISM: Artificial Sequence
<220> FEATURE:
<223> OTHER INFORMATION: Synthetic

<400> SEQUENCE: 23
ggtcactgca tggggcaggc tggtggggag aaggtcaatg                             40

<210> SEQ ID NO 24
<211> LENGTH: 40
<212> TYPE: DNA
<213> ORGANISM: Artificial Sequence
<220> FEATURE:
<223> OTHER INFORMATION: Synthetic

<400> SEQUENCE: 24
ggtcactgca tggggcaggc tggtggggag aaggtcaagg                             40

<210> SEQ ID NO 25
<211> LENGTH: 40
<212> TYPE: DNA
<213> ORGANISM: Artificial Sequence
<220> FEATURE:
<223> OTHER INFORMATION: Synthetic

<400> SEQUENCE: 25
tttgtttgta atatactgct ctctcctgat ttggtccagg                             40

<210> SEQ ID NO 26
<211> LENGTH: 40
<212> TYPE: DNA

```
<213> ORGANISM: Artificial Sequence
<220> FEATURE:
<223> OTHER INFORMATION: Synthetic

<400> SEQUENCE: 26
tttgtttgta atatactgct ctctcctgat ttggtccaag                    40

<210> SEQ ID NO 27
<211> LENGTH: 40
<212> TYPE: DNA
<213> ORGANISM: Artificial Sequence
<220> FEATURE:
<223> OTHER INFORMATION: Synthetic

<400> SEQUENCE: 27
gggtcaagtt agggaaaagc cactcccaca catttcatgg                    40

<210> SEQ ID NO 28
<211> LENGTH: 40
<212> TYPE: DNA
<213> ORGANISM: Artificial Sequence
<220> FEATURE:
<223> OTHER INFORMATION: Synthetic

<400> SEQUENCE: 28
gagtcaagtt agggaaaagc cactcccaca catttcatgg                    40

<210> SEQ ID NO 29
<211> LENGTH: 40
<212> TYPE: DNA
<213> ORGANISM: Artificial Sequence
<220> FEATURE:
<223> OTHER INFORMATION: Synthetic

<400> SEQUENCE: 29
gtgcgacaga ttcctacagc caccatctac agaataaaga                    40

<210> SEQ ID NO 30
<211> LENGTH: 40
<212> TYPE: DNA
<213> ORGANISM: Artificial Sequence
<220> FEATURE:
<223> OTHER INFORMATION: Synthetic

<400> SEQUENCE: 30
gtgtgacaga ttcctacagc caccatctac agaataaaga                    40

<210> SEQ ID NO 31
<211> LENGTH: 30
<212> TYPE: DNA
<213> ORGANISM: Artificial Sequence
<220> FEATURE:
<223> OTHER INFORMATION: Synthetic

<400> SEQUENCE: 31
cctgaaaaaa aaatcaggag agagcagtat                               30

<210> SEQ ID NO 32
<211> LENGTH: 34
<212> TYPE: DNA
<213> ORGANISM: Artificial Sequence
<220> FEATURE:
<223> OTHER INFORMATION: Synthetic

<400> SEQUENCE: 32
gtgtgggagt ggcttttccc tttttttttt accc                          34
```

<210> SEQ ID NO 33
<211> LENGTH: 29
<212> TYPE: DNA
<213> ORGANISM: Artificial Sequence
<220> FEATURE:
<223> OTHER INFORMATION: Synthetic

<400> SEQUENCE: 33
cattcccccc tccccaccag cctgcccca                               29

<210> SEQ ID NO 34
<211> LENGTH: 36
<212> TYPE: DNA
<213> ORGANISM: Artificial Sequence
<220> FEATURE:
<223> OTHER INFORMATION: Synthetic

<400> SEQUENCE: 34
tagatggtgg ctgtaggaat aaaaaaaaaa aagcac                       36

<210> SEQ ID NO 35
<211> LENGTH: 450
<212> TYPE: DNA
<213> ORGANISM: Artificial Sequence
<220> FEATURE:
<223> OTHER INFORMATION: Synthetic

<400> SEQUENCE: 35
ttgccctagt ctttgcatcc aactcatgaa aaaaagcatc tttaaaaagc cagtttctgc    60
tgacttgcaa aaagagcaaa atctaggtga aatgtattgt ttaaactttg attaccaacc   120
ttgaaaagga acatattaac cagtgtcttc tgataagcag atcacttgcc tcatgtctta   180
gaatccagta ggtggcccct tggccatgaa atgtgtggga gtggcttttc cctaacttga   240
cccttctttc agtgggaggg aactattgag aggaacaaag agcttataaa tacattagga   300
cctggaattc ggttgtccag ccacaaaggt gacagcattt aacaaagtaa gtactgatct   360
tataaatctc tctacattgc ctcacaccct cctctctagc ctcctagaaa aatacactaa   420
tatgtgtcct tagcacaaga aaaagtttgt                                   450

<210> SEQ ID NO 36
<211> LENGTH: 450
<212> TYPE: DNA
<213> ORGANISM: Artificial Sequence
<220> FEATURE:
<223> OTHER INFORMATION: Synthetic

<400> SEQUENCE: 36
ttgccctagt ctttgcatcc aactcatgaa aaaaagcatc tttaaaaagc cagtttctgc    60
tgacttgcaa aaagagcaaa atctaggtga aatgtattgt ttaaactttg attaccaacc   120
ttgaaaagga acatattaac cagtgtcttc tgataagcag atcacttgcc tcatgtctta   180
gaatccagta ggtggcccct tggccatgaa atgtgtggga gtggcttttc cctaacttga   240
ctcttctttc agtgggaggg aactattgag aggaacaaag agcttataaa tacattagga   300
cctggaattc ggttgtccag ccacaaaggt gacagcattt aacaaagtaa gtactgatct   360
tataaatctc tctacattgc ctcacaccct cctctctagc ctcctagaaa aatacactaa   420
tatgtgtcct tagcacaaga aaaagtttgt                                   450

<210> SEQ ID NO 37

```
<211> LENGTH: 22
<212> TYPE: DNA
<213> ORGANISM: Artificial Sequence
<220> FEATURE:
<223> OTHER INFORMATION: Synthetic

<400> SEQUENCE: 37
tcatgtctta gaatccagta gg                                              22

<210> SEQ ID NO 38
<211> LENGTH: 19
<212> TYPE: DNA
<213> ORGANISM: Artificial Sequence
<220> FEATURE:
<223> OTHER INFORMATION: Synthetic

<400> SEQUENCE: 38
gtgaggcaat gtagagaga                                                  19

<210> SEQ ID NO 39
<211> LENGTH: 40
<212> TYPE: DNA
<213> ORGANISM: Artificial Sequence
<220> FEATURE:
<223> OTHER INFORMATION: Synthetic

<400> SEQUENCE: 39
agttccctcc cactgaaaga agccttggcc atgaaatgtg                            40

<210> SEQ ID NO 40
<211> LENGTH: 47
<212> TYPE: DNA
<213> ORGANISM: Artificial Sequence
<220> FEATURE:
<223> OTHER INFORMATION: Synthetic

<400> SEQUENCE: 40
acattaggac ctggaattcg gttacttact ttgttaaatg ctgtcac                   47

<210> SEQ ID NO 41
<211> LENGTH: 4
<212> TYPE: DNA
<213> ORGANISM: Artificial Sequence
<220> FEATURE:
<223> OTHER INFORMATION: Synthetic

<400> SEQUENCE: 41 accc                                                                   4

<210> SEQ ID NO 42
<211> LENGTH: 24
<212> TYPE: DNA
<213> ORGANISM: Artificial Sequence
<220> FEATURE:
<223> OTHER INFORMATION: Synthetic

<400> SEQUENCE: 42
agtggctttt ccctaacttg accc                                            24

<210> SEQ ID NO 43
<211> LENGTH: 23
<212> TYPE: DNA
<213> ORGANISM: Artificial Sequence
<220> FEATURE:
<223> OTHER INFORMATION: Synthetic

<400> SEQUENCE: 43
```

```
ggaacatatt aaccagtgtc ttc                                              23

<210> SEQ ID NO 44
<211> LENGTH: 18
<212> TYPE: DNA
<213> ORGANISM: Artificial Sequence
<220> FEATURE:
<223> OTHER INFORMATION: Synthetic

<400> SEQUENCE: 44
accgaattcc aggtccta                                                    18
```

OLIGONUCLEOTIDE PROBE FOR DETECTING SINGLE NUCLEOTIDE POLYMORPHISM, AND METHOD FOR DETECTING SINGLE NUCLEOTIDE POLYMORPHISM

SEQUENCE LISTING SUBMISSION VIA EFS-WEB

A computer readable text file, entitled "SequenceListing.txt" created on or about Jun. 15, 2017, with a file size of about 10 kb contains the sequence listing for this application and is hereby incorporated by reference in its entirety.

TECHNICAL FIELD

The present invention relates to an oligonucleotide probe for detecting a single nucleotide polymorphism, and a method for detecting a single nucleotide polymorphism.

BACKGROUND ART

A difference of some sort found at a prescribed frequency in a sequence of a nucleic acid at the genetic level of multicellular organisms such as mammals and organisms such as bacterium and viruses is designated as a genetic mutation. The difference in the sequence of a nucleic acid is caused by replacement, insertion, deletion or recombination. Among such differences in the sequence, a mutation present at a frequency of 1% or more in a given population is particularly designated as a genetic polymorphism.

Among genetic polymorphisms, a polymorphism caused by replacement of one base in a sequence is particularly designated as a single nucleotide polymorphism (hereinafter sometimes abbreviated as the "SNP"). The SNP is attracting attention because the appearance frequency thereof is the highest among those of mutations found in the human genome. In other words, it is expected that much information can be obtained by analyzing the relationship between the presence/absence of a polymorphism and a phenotype if information on the position of a genetic polymorphism and the variation is accumulated so as to compare a gene of an individual with a wild-type gene having a normal phenotype.

Besides, since the genetic polymorphism spreads in a population at a prescribed frequency, it is attracting attention as one causing no change in trait, or one affecting not a trait particularly disadvantageous for viability (reproduction) but a trait that can be called a constitution. For example, it is known that susceptibility to a lifestyle-related disease such as diabetes, hypertension or obesity, an immune-mediated disease such as rheumatism or allergy, or a disease such as a cancer is affected by a polymorphism. Besides, drug metabolism (drug effectiveness), human leukocyte histocompatibility antigen and the like are regarded to be controlled in accordance with a polymorphism. Furthermore, it is regarded that the drug resistance not only of a human but also of some bacterium is determined by an SNP occurring in a specific gene. Therefore, SNP analysis is expected to be useful for personalized medicine in which an optimal drug in accordance with the genetic type of an individual is administered, and for identification of multidrug resistant pathogens recently at issue.

Various detection methods and detection probes for the SNP have been developed so far. An example of the detection methods includes a fluorescence labeled probe method. In this method, it is determined whether or not the SNP is present in a sequence of a target nucleic acid depending on a difference in the hybridization efficiency attained when a fluorescence labeled probe is perfectly matched or mismatched with the target nucleic acid. Accordingly, although the detection sensitivity for the SNP is increased as the probe is shorter, if the probe is too short, there arises a problem that the binding force to the target sequence is lowered and hence the probe does not hybridize. In order to overcome this problem, a fluorescence labeled probe comprising a region for detecting the SNP, a region for recognizing a sequence in the vicinity of the SNP and a region for connecting these two regions to each other has been developed (Patent Literatures 1 and 2).

Patent Literature 1 discloses an oligonucleotide comprising: a switch domain comprising (a) a nucleic acid region complementary to a first sequence of nucleic acid residues of a target nucleic acid and (b) at least one cross-linking domain and at least one binding domain, in which the switch domain is capable of distinguishing (i) a second sequence of the nucleic acid residues of the target nucleic acid complementary to the binding domain from (ii) a second sequence of the nucleic acid residues of the target nucleic acid comprising at least one nucleic acid residue not complementary to the binding domain under a condition where the region (a) forms a stable double strand together with the first sequence of the nucleic acid residues of the target nucleic acid. Besides, Patent Literature 1 states that the cross-linking domain comprises a universal base, a non-hydrogen bonding natural base or an analog of any of these, or a mixture of a universal base and a non-hydrogen bonding natural base or an analog of any of these.

Patent Literature 2 discloses a detectably labeled probe, comprising an anchor nucleic acid domain and a reporter nucleic acid domain, in which the anchor and reporter domains are linked to each other via a non-nucleoside linker, neither the anchor domain nor the reporter domain forms a stem loop in the absence of a target nucleic acid, (i) the probe is not extended by polymerase, (ii) the linker is bound to the anchor domain within two nucleotides at the 3'-end of the anchor domain, and is bound to the reporter domain within two nucleotides at the 5'-end of reporter domain, and the anchor domain is not bound to a detectable label.

CITATION LIST

Patent Literature

Patent Literature 1: Japanese Unexamined Patent Publication No. 2006-525027
Patent Literature 2: Japanese Unexamined Patent Publication No. 2013-501508

SUMMARY OF INVENTION

Technical Problem

In the oligonucleotide described in Patent Literature 1, however, the cross-linking domain is required to have a universal base or the like for forming a prescribed structure. Therefore, problems of this oligonucleotide are that it lacks flexibility with respect to probe design, and in addition, that it is more expensive than a case where usual bases alone are used in the oligonucleotide synthesis. Besides, since the probe described by Patent Literature 2 uses the non-nucleotide linker, it is necessary to prepare the linker separately from the anchor nucleic acid domain and the reporter nucleic acid domain, and to synthesize these thereafter, and therefore, there arises a problem that the synthesis of the probe is troublesome.

Therefore, an object of the present invention is to provide an oligonucleotide probe for detecting a single nucleotide polymorphism that can be simply and inexpensively synthesized and can detect the presence of an SNP with accuracy and sensitivity. Another object of the present invention is to provide a method for detecting a single nucleotide polymorphism using the oligonucleotide probe.

Solution to Problem

The present invention provides an oligonucleotide probe for single nucleotide polymorphism detection to be used for a target nucleic acid where a single nucleotide polymorphism is present, wherein the target nucleic acid comprises a first target sequence corresponding to a region where the single nucleotide polymorphism is present, and a second target sequence positioned on a 3' or 5' side of the first target sequence and corresponding to a region where the single nucleotide polymorphism is absent, the probe comprises a reporter region for detecting the single nucleotide polymorphism, an anchor region, and a linker region, the reporter region comprises an oligonucleotide consisting of a sequence perfectly matching with the first target sequence when a nucleotide of the single nucleotide polymorphism is a first nucleotide, and mismatching with the first target sequence when the nucleotide of the single nucleotide polymorphism is a nucleotide other than the first nucleotide; and a fluorescent dye quenching when the first target sequence and the reporter region hybridize, the anchor region comprises an oligonucleotide consisting of a sequence complementary to the second target sequence, and the linker region links the reporter region and the anchor region to each other, and comprises an oligonucleotide consisting of a sequence non-complementary to a sequence disposed between the first target sequence and the second target sequence in the target nucleic acid.

The probe of the present invention comprises, separately from the reporter region for detecting an SNP, the anchor region binding to the target sequence regardless of the presence of the SNP, and hence the binding property of the probe can be attained. Therefore, in the probe of the present invention, the reporter region can be designed to be shorter for detecting the SNP with accuracy. In other words, the probe of the present invention can more accurately and sensitively detect an SNP than a usual probe. Besides, since the probe of the present invention is constituted by an oligonucleotide, the probe can be simply and inexpensively synthesized.

A length of the oligonucleotide of the reporter region is preferably shorter than a length of the oligonucleotide of the anchor region. Thus designed reporter region and anchor region tend to achieve both a good binding property of the probe to the target nucleic acid, and high accuracy and detection sensitivity in SNP detection.

The linker region is preferably an oligonucleotide consisting of a sequence not comprising a universal base. When no universal base is used in the linker region, the probe can be more inexpensively synthesized.

The linker region is preferably an oligonucleotide consisting of only one kind of base selected from adenine, guanine, cytosine and thymine Thus, the possibility that the linker region of the probe binds to the target nucleic acid is lowered, and hence, the flexibility of the reporter region is increased, and the SNP detectability can be further improved. Besides, if the linker region is constituted by the above-described base alone, the probe can be more inexpensively synthesized.

The linker region is preferably an oligonucleotide consisting of 3 to 11 nucleotides. Thus, the anchor region binding to the target nucleic acid is spaced by a prescribed distance from the reporter region, and hence, the flexibility of the reporter region is increased and the SNP detectability can be further improved.

The present invention also provides a method for single nucleotide polymorphism detection, comprising: preparing a mixture by mixing the above-described probe of the present invention and a target nucleic acid where the single nucleotide polymorphism is present; measuring fluorescence intensity of the mixture; and detecting the presence/absence of the single nucleotide polymorphism in the target nucleic acid on the basis of the fluorescence intensity.

According to the method of the present invention, since the probe of the present invention is used, an SNP can be more accurately and sensitively detected based on the fluorescence intensity than in using a usual probe.

Advantageous Effects of Invention

According to the present invention, an oligonucleotide probe for single nucleotide polymorphism detection that can be simply and inexpensively synthesized and can accurately and sensitively detect the presence of an SNP can be provided. The present invention also can provide a method for detecting a single nucleotide polymorphism using the oligonucleotide probe.

BRIEF DESCRIPTION OF DRAWINGS

FIG. 3 illustrates the results of the Tm analysis obtained by using linker type SNP-oligo-DNAs.

FIG. 5 illustrates the results of the Tm analysis obtained by using a linker type QProbe binding probe for various synthesized DNAs.

DESCRIPTION OF EMBODIMENTS

Figure 1A:
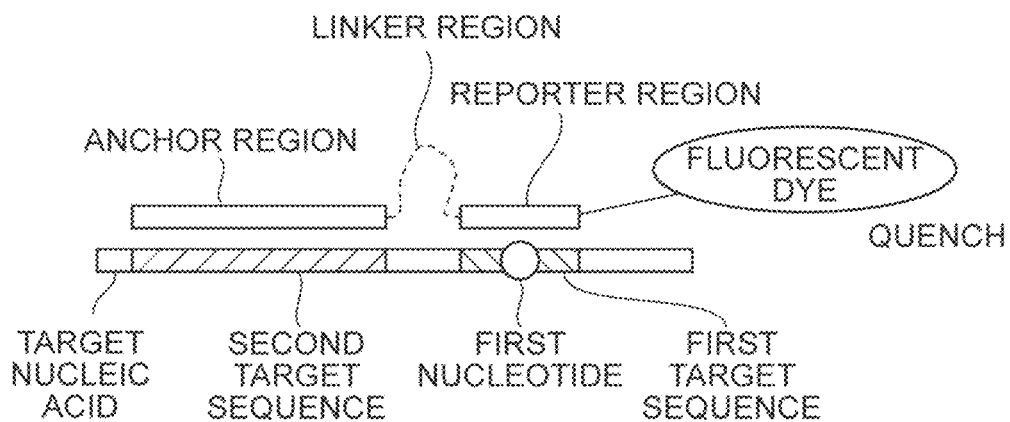
FIG. 1 is a schematic diagram of a mechanism for SNP detection using a probe of the present invention.

Embodiments of the present invention (hereinafter referred to as the "present embodiment") will now be described in detail. It is noted that the present invention is not limited to the following embodiments.

Herein, the term "single nucleotide polymorphism (SNP)" refers to a polymorphism caused by replacement of one base in a sequence.

Herein, the term "target nucleic acid" refers to a nucleic acid to be checked for the presence/absence of an SNP by using a probe of the present embodiment. The target nucleic acid comprises a first target sequence corresponding to a region where the SNP is present, and a second target sequence not overlapping the first target sequence, disposed on the 3' or 5' side of the first target sequence, and corresponding to a region where the SNP is absent.

Herein, the term "perfect match" means that a sequence of a reporter region is perfectly complementary to the first target sequence of the target nucleic acid and hence the first target sequence and the reporter region hybridize. On the contrary, the term "mismatch" means that the sequence of the reporter region is different, even in one base, to the first target sequence of the target nucleic acid and hence the first target sequence and the reporter region cannot hybridize.

The target nucleic acid comprises the first target sequence and the second target sequence. The first target sequence and the second target sequence can be precedently determined on the basis of a sequence of a nucleic acid in which the SNP is known to be present.

The first target sequence is preferably a region, comprised in the sequence of the nucleic acid in which the SNP is known to be present and consisting of 3 to 6 nucleotides including a base where the SNP desired to be detected can occur. The first target nucleic acid is more preferably a region consisting of 3 to 5 nucleotides, and further preferably a region consisting of 4 nucleotides. In the first target sequence, the position of the base where the SNP can occur is not especially limited, and is preferably in the vicinity of the center of the first target sequence.

The second target sequence is preferably a region not overlapping the first target sequence, disposed on the 3' or 5' side of the first target sequence, and consisting of 10 to 20 nucleotides in a region where the SNP is absent. The second target sequence is more preferably a region consisting of 12 to 18 nucleotides, and further preferably a region consisting of 15 nucleotides.

If the second target sequence is positioned on the 3' side of the first target sequence, the number of nucleotides (an interval) disposed between the 3'-end of the first target sequence and the 5'-end of the second target sequence is preferably 0 to 15, more preferably 3 to 12, and further preferably 4 to 10. If the distance between the first target sequence and the second target sequence is set to fall in the above-described range, an appropriate distance can be retained between a reporter region and an anchor region of a probe according to the present embodiment, and therefore, the SNP detectability tends to be improved. Besides, since the length of a linker region can be set in accordance with the distance between the first target sequence and the second target sequence, there is no need to synthesize an unnecessary nucleotide, and hence it also tends to be economically advantaged. If the second target sequence is positioned on the 5' side of the first target sequence, the number of nucleotides disposed between the 5'-end of the first target sequence and the 3'-end of the second target sequence can be set to fall in the above-described range.

Examples of the target nucleic acid of the present embodiment include a DNA and an RNA. The origin of the target nucleic acid is not especially limited as long as a DNA or an RNA is comprised, and examples include animals, plants, fungi, microorganisms and viruses. Besides, a preparation method for the target nucleic acid is also not especially limited, and it may be prepared directly from an organism or a virus, may be prepared from a specific tissue, may be prepared by artificial cloning from a nucleic acid used as a template, or may be prepared by using an amplification product obtained by a PCR method or a LAMP method.

<Probe>

The probe of the present embodiment comprises the reporter region detecting a single nucleotide polymorphism, the anchor region, and the linker region. In the probe of the present embodiment, the positional relationship between the reporter region and the anchor region can be appropriately set in accordance with the positional relationship between the first target sequence and the second target sequence set in the target nucleic acid. For example, if the second target sequence is positioned on the 3' side of the first target sequence, the anchor region is disposed on the 5' side of the reporter region.

Since the probe of the present embodiment comprises, separately from the reporter region for detecting an SNP, the anchor region binding to the target sequence regardless of the presence of the SNP, the binding property of the probe can be attained. Therefore, the reporter region for accurate SNP detection can be designed to be shorter. Accordingly, the probe of the present embodiment can more accurately and sensitively detect the SNP than a usual probe.

A method for producing the probe of the present embodiment is not especially limited, and an example includes a usual oligonucleotide synthesis method employing chemical synthesis. The probe of the present embodiment is constituted by a usual oligonucleotide and hence can be simply and inexpensively produced without employing a complicated synthesis method.

(Reporter Region)

The reporter region is a region for detecting an SNP. The reporter region is an oligonucleotide consisting of a sequence perfectly matching with the first target sequence if a nucleotide of the single nucleotide polymorphism is a first nucleotide, and mismatching with it if the nucleotide of the single nucleotide polymorphism is a nucleotide other than the first nucleotide. Herein, the term "first nucleotide" refers to a base where the SNP desired to be detected can occur in a target nucleic acid. For example, if the first nucleotide is a nucleotide of the target nucleic acid where the SNP is absent, the reporter region perfectly matches with the first target sequence when the SNP is absent and hence hybridizes, and mismatches when the SNP is present and hence does not hybridize.

Besides, the reporter region comprises a fluorescent dye that quenches when the first target sequence and the reporter region hybridize. Since the reporter region comprises such a fluorescent dye, the SNP can be simply detected by measuring the fluorescence intensity. Examples of the fluorescent dye having such a characteristic include QProbe series (manufactured by Nippon Steel & Sumikin Eco-Tech Corporation). If guanine is present in the vicinity of a base complementary to a base modified with the fluorescent dye when the probe hybridizes, fluorescence resonance energy transfer occurs and hence the fluorescence quenches in the QProbe. Specific examples of the fluorescent dye comprised in the QProbe include FITC, TMR, 6-joe, Bodipy-FL/C6 and Bodipy-FL/C3. When such a fluorescent dye is used, the fluorescent characteristic varies depending on whether or not the reporter region and the first target sequence hybridize. Therefore, the probe of the present embodiment is economically excellent because there is no need to add a quencher as in a usual SNP detection method using a probe comprising a fluorescent dye. The fluorescent dye is preferably bound to an end of the reporter region opposite to the linker region.

The oligonucleotide of the reporter region is a nucleotide consisting of a sequence complementary to the first target sequence excluding a nucleotide corresponding to the first nucleotide. The nucleotide corresponding to the first nucleotide can be appropriately set by a user depending on whether, in using the probe of the present embodiment, the probe preferably quenches when the SNP is present or preferably quenches when the SNP is absent. If the probe preferably quenches when the SNP is present, the nucleotide corresponding to the first nucleotide is selected as a nucleotide complementary to the first nucleotide of the target nucleic acid where the SNP is present. Alternatively, if the probe preferably quenches when the SNP is absent, the nucleotide corresponding to the first nucleotide is selected as a nucleotide complementary to the first nucleotide of the target nucleic acid where the SNP is absent.

From the viewpoint of further improving the SNP detectability, the length of the oligonucleotide of the reporter region is preferably 3 to 6 nucleotides, more preferably 3 to 5 nucleotides, and further preferably 4 nucleotides. Besides, from the viewpoint of attaining, in the probe of the present embodiment, both good binding property to the target nucleic acid and good SNP detectability, the length of the oligonucleotide of the reporter region is preferably shorter than the length of an oligonucleotide of the anchor region. From the viewpoint that the reporter region hybridize to the target nucleic acid for quenching the fluorescence of the fluorescent dye, the oligonucleotide of the reporter region is preferably designed so that guanine is present in the first target sequence within 1 to 3 bases from the binding portion of the fluorescent dye.

(Anchor Region)

The anchor region is a region for causing the probe to bind to the target nucleic acid no matter whether the SNP is present/absent in the target nucleic acid. The anchor region has an oligonucleotide consisting of a sequence complementary to the second target sequence. From the viewpoint of attaining good binding property to the second target sequence, the length of the oligonucleotide of the anchor region is preferably 10 to 20 nucleotides, more preferably 12 to 18 nucleotides, and further preferably 15 nucleotides.

(Linker Region)

The linker region is a region for increasing the flexibility of the probe. The linker region links the reporter region and the anchor region to each other. The linker region has an oligonucleotide consisting of a sequence non-complementary to a sequence disposed between the first target sequence and the second target sequence in the target nucleic acid.

From the viewpoint that the probe can be more inexpensively synthesized, the linker region preferably comprises no universal base. Examples of the universal base include universal bases that are bases other than adenine, guanine, cytosine, thymine and uracil, and analogs thereof. Examples of the universal bases and the analogs thereof include 5-nitroindole, deoxyriboside, 3-nitropyrrole deoxyriboside, 4-nitrobenzimidazole deoxyriboside, deoxynebularine, deoxyinosine, 2'-OMe inosine, 2'-OMe 5-nitroindole riboside, 2'-OMe 3-nitropyrrole riboside, 2'-F inosine riboside, 2'-F nebularine, 2'-F 5-nitroindole riboside, 2'-F 4-nitrobenzimidazole riboside, 2'-F 3-nitropyrrole ribo side, PNA-5-nitroindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'-O-methoxyethyl nebularine, 2'-O-methoxyethyl 5-nitroindole riboside, 2'-O-methoxyethyl 4-nitro-benzimidazole riboside, 2'-O-methoxyethyl 3-nitropyrrole riboside, and deoxy $R_p$MP-5-nitroindole dimer 2'-OMe $R_p$MP-5-nitroindole dimer.

The linker region is preferably an oligonucleotide consisting of only one kind of base selected from adenine, guanine, cytosine and thymine Thus, the possibility of causing the linker region to bind to the target nucleic acid is lowered, and hence, the flexibility of the reporter region is increased, and the SNP detectability can be easily improved. Besides, if the linker region consists of the above-described base alone, there is a tendency that the probe can be more inexpensively synthesized.

Besides, the length of the oligonucleotide of the linker region is preferably 3 to 11 nucleotides, and more preferably 3 to 9 nucleotides. If the length of the oligonucleotide of the linker region falls in the above-described range, the anchor region binding to the target nucleic acid is spaced by a prescribed distance from the reporter region, and hence, the flexibility of the reporter region is increased and the SNP detectability tends to be improved. Besides, from the viewpoint of attaining the flexibility in the conformational structure in hybridization of the target nucleic acid and the probe of the present embodiment, the length of the oligonucleotide of the linker region is preferably −5 to +5 nucleotides, and more preferably −3 to +3 nucleotides as compared with the distance (the interval) between the first target sequence and the second target sequence.

<Method for Detecting Single Nucleotide Polymorphism Using Probe>

Since the probe of the present embodiment comprises the fluorescent dye in the reporter region which detects an SNP, the presence/absence of the SNP in the target nucleic acid can be detected.

An embodiment of a method for SNP detection is, for example, a method including preparing a mixture by mixing the probe of the present embodiment and a target nucleic acid where an SNP is present, measuring the fluorescence intensity of the mixture, and detecting the presence/absence of the SNP (single nucleotide polymorphism) in the target nucleic acid on the basis of the measured fluorescence intensity.

Figure 1B:
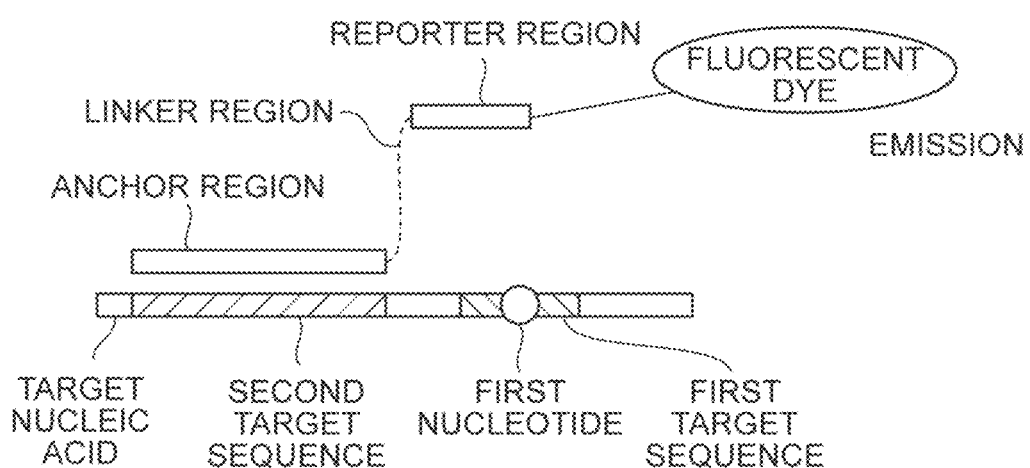

FIG. 1 is a schematic diagram illustrating states of the probe of the present embodiment and the target nucleic acid when they are mixed. The probe hybridizes to the target nucleic acid in the anchor region. In the case of perfect match where the reporter region has a sequence complementary to the first target sequence, the reporter region hybridizes to the first target sequence, and hence the fluorescence of the fluorescent dye quenches (FIG. 1(a)). On the other hand, in the case of mismatch where the reporter region does not have a sequence complementary to the first target sequence, the reporter region cannot hybridize to the first target sequence, and hence the fluorescence of the fluorescent dye is continuously emitted (FIG. 1(b)). The probe of the present embodiment emits the fluorescence if the reporter region does not hybridize to the target nucleic acid. Accordingly, for example, in a case where the first nucleotide is the nucleotide of the target nucleic acid where the SNP is absent, if the fluorescence intensity of the mixture obtained by mixing the probe and the target nucleic acid is reduced as compared with that before mixing, it can be determined that the SNP is absent in the target nucleic acid. Alternatively, in a case where the first nucleotide is the nucleotide of the target nucleic acid where the SNP is present, if the fluorescence intensity of the mixture obtained by mixing the probe and the target nucleic acid is reduced as compared with that before mixing, it can be determined that the SNP is present in the target nucleic acid. According to the method of the present embodiment, the presence/absence of an SNP can be measured at room temperature (about 25° C.), and therefore, the SNP analysis can be efficiently performed.

Another embodiment of the method for SNP detection is, for example, a method of performing Tm (Melting Temperature) analysis. The Tm analysis can be performed by a method usually employed by those skilled in the art. The Tm analysis can be performed, for example, by a method in which the probe and the target nucleic acid are mixed, and the fluorescence intensity of a mixture thus obtained is measured while lowering the temperature of the mixture. If the reporter region mismatches with the first target sequence, the thermal stability of a complex of the probe and the target nucleic acid is lower than in the case of perfect match, and hence, the reporter region binds to the target nucleic acid and the fluorescence quenching is observed at a lower temperature. The temperature at this time is designated as a quenching start temperature. On the other hand, if the reporter region perfectly matches with the first target sequence, the thermal stability of the complex of the probe and the target nucleic acid is higher than in the case of the mismatch, and hence, the reporter region binds to the target nucleic acid and the fluorescence quenching is observed even at a higher temperature. Accordingly, for example, in a case where the reporter region is designed to perfectly match when the SNP is absent, the quenching start temperature of the target nucleic acid where the SNP is present is measured, and if a quenching start temperature is higher than this value, it can be determined that the SNP is absent in the target nucleic acid used in the measurement.

Since the probe of the present embodiment hybridizes to the target nucleic acid in the anchor region, the length of the nucleotide of the reporter region which detects an SNP can be made very short. Therefore, the specificity of the reporter region becomes high, and hence, the reporter region is difficult to hybridize to a mismatched sequence under a low temperature condition such as room temperature. As a result, in the case of the mismatch, the fluorescence intensity of the mixture at around room temperature is not conspicuously lowered as compared with the fluorescence intensity at the quenching start temperature. On the other hand, in the case where the reporter region perfectly matches, the reporter region hybridizes to the target nucleic acid at around room temperature. Therefore, in the case of the perfect match, the fluorescence intensity of the mixture at around room temperature is conspicuously lowered as compared with the fluorescence intensity at the quenching start temperature, and is about 60% or lower. Accordingly, in the SNP detection method employing the Tm analysis, for example, if the reporter region is designed to perfectly match when the SNP is absent, it can be determined that the SNP is absent in the target nucleic acid when the fluorescence intensity of the mixture at around room temperature is 60% or lower as compared with the fluorescence intensity at the quenching start temperature.

In the method for detecting an SNP of the present embodiment, an amplification product amplified by the PCR method, the LAMP method or the like can be used as the target nucleic acid.

EXAMPLES

The present invention will now be described more specifically with reference to Examples, and it is noted that the present invention is not limited to these Examples. In the following Examples, PM stands for perfect match, and MM stands for mismatch.

Example 1: Effect of Addition of Linker Region

An effect of linking a reporter region and an anchor region via a linker region was verified. As a detection system, a system for detecting a missense mutation of replacement of 516 Asp (GAC) by Val (GTC) in rpoB gene of *Mycobacterium Tuberculosis* was used. Change in a fluorescence value caused in hybridization, to a QProbe binding DNA, of an SNP-oligo-DNA or a linker type SNP-oligo-DNA having a length changed in a stepwise manner was analyzed. Since the QProbe binding DNA comprises an SNP, a system in which the SNP-oligo-DNA or the linker type SNP-oligo-DNA can detect the SNP in case of perfect match and cannot detect the SNP in case of mismatch was employed.

(Materials)

QProbe binding DNA: DNA having a sequence of SEQ ID NO: 1 bound to QProbe-3G (manufactured by Nippon Steel & Sumikin Eco-Tech Corporation).

SNP-oligo-DNA: DNA having a sequence of any one of SEQ ID NOS: 2 to 11.

Linker type SNP-oligo-DNA: DNA having a sequence of any one of SEQ ID NOS: 12 to 21.

Adenine was used as the linker.

Hybridization buffer: 50 mM KCl, 10 mM Tris-HCl (pH 8.0), 1.5 mM $MgCl_2$, 0.1% TWEEN-20.

The characteristics of the SNP-oligo-DNAs and the linker type SNP-oligo-DNAs are shown in Tables 1 and 2.

TABLE 1

| | SNP-Oligo-DNA | | | | | | | | | |
|---|---|---|---|---|---|---|---|---|---|---|
| SEQ ID NO: | 2 | 3 | 4 | 5 | 6 | 7 | 8 | 9 | 10 | 11 |
| Length of Oligo DNA | 6 | 6 | 7 | 7 | 8 | 8 | 9 | 9 | 10 | 10 |
| SNP Detection | PM | MM | PM | MM | PM | MM | PM | MM | PM | MM |

TABLE 2

| | Linker type SNP-Oligo DNA | | | | | | | | | |
|---|---|---|---|---|---|---|---|---|---|---|
| SEQ ID NO: | 12 | 13 | 14 | 15 | 16 | 17 | 18 | 19 | 20 | 21 |
| Length of Oligo DNA | 20 | 20 | 22 | 22 | 24 | 24 | 26 | 26 | 28 | 28 |
| Length of Reporter Region | 4 | 4 | 4 | 4 | 4 | 4 | 4 | 4 | 4 | 4 |

TABLE 2-continued

| | Linker type SNP-Oligo DNA | | | | | | | | | |
|---|---|---|---|---|---|---|---|---|---|---|
| SEQ ID NO: | 12 | 13 | 14 | 15 | 16 | 17 | 18 | 19 | 20 | 21 |
| Length of Anchor Region | 15 | 15 | 15 | 15 | 15 | 15 | 15 | 15 | 15 | 15 |
| Length of Linker Region | 1 | 1 | 3 | 3 | 5 | 5 | 7 | 7 | 9 | 9 |
| SNP Detection | PM | MM | PM | MM | PM | MM | PM | MM | PM | MM |

(Method)

A sample was prepared by mixing 0.1 μL, of 10 μM QProbe binding DNA, 3.2 μL, of 10 μM SNP-oligo-DNA or 10 μM linker type SNP-oligo-DNA and 16.7 μL of the hybridization buffer, and dispensing the resultant mixture into an 8-tube strip by 20 μL each. The sample was subjected to the Tm analysis using Mx3005P Real-Time PCR System (manufactured by Agilent Technologies) so as to measure the fluorescence intensity while lowering the temperature from 99° C. to 25° C. The temperature drop rate was set to −2° C./30 seconds.

(Results)

Figures 2A, 2B, 2C, 2D, 2E:
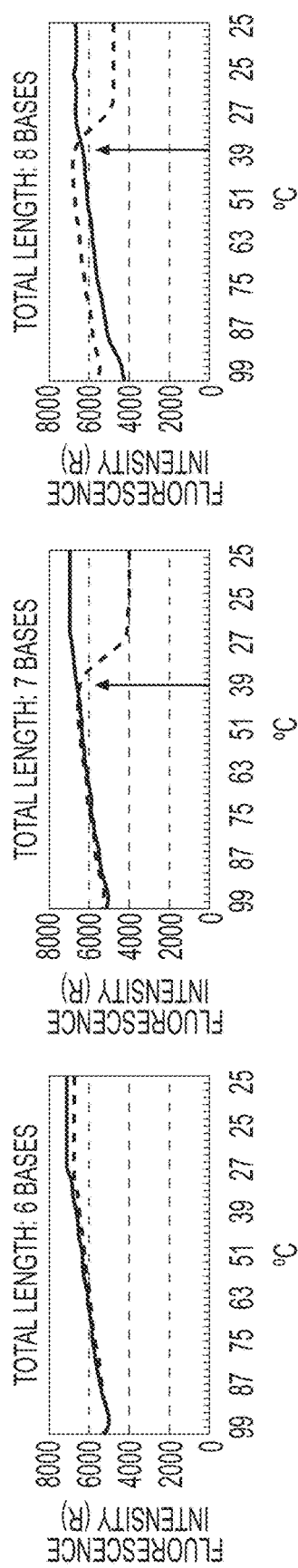
FIG. 2 illustrates the results of Tm analysis obtained by using SNP-oligo-DNAs.
Figure 4A:
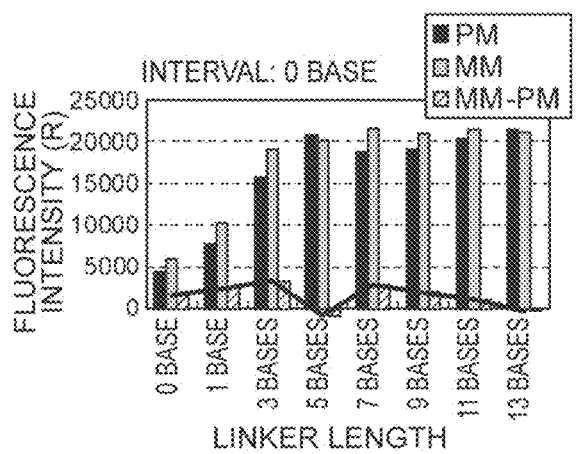
FIG. 4 illustrates the results of the Tm analysis obtained by using a linker type SNP-oligo-DNA performed at 25° C. with the length of an interval and the length of a linker changed.
Figure 4D:
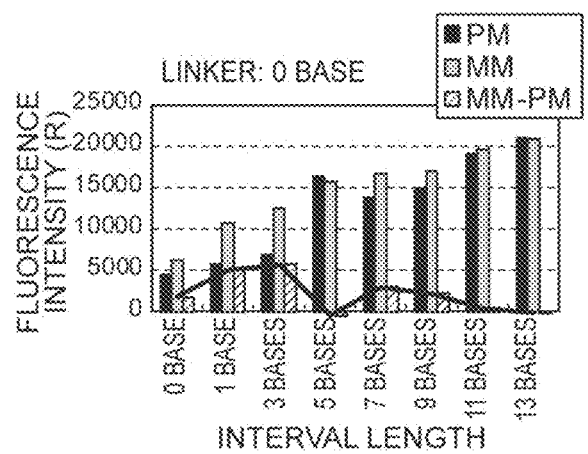
Figure 4B:
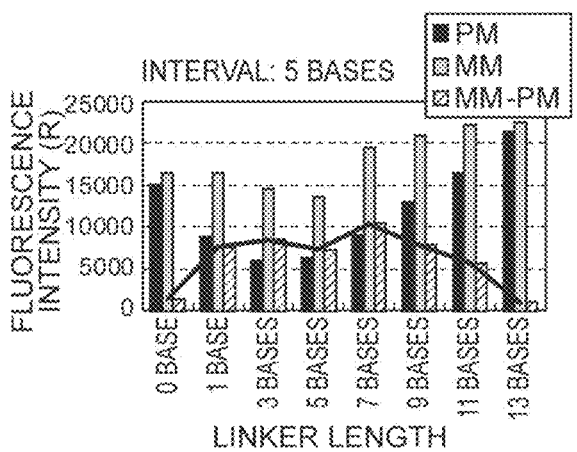
Figure 4E:
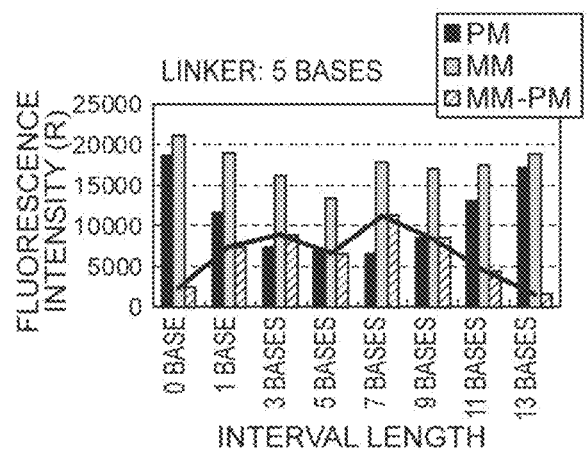
Figure 4C:
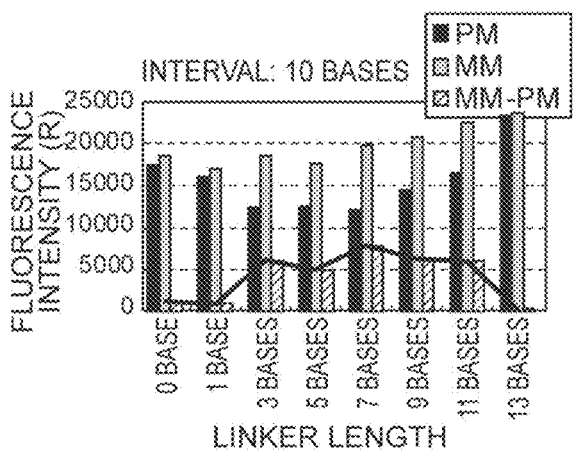
Figure 4F:
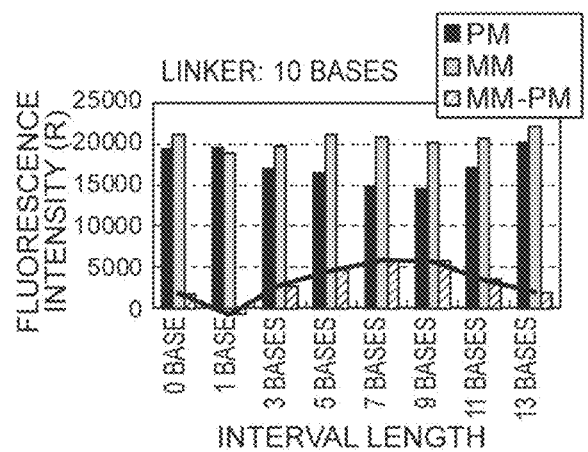

The results obtained by using the SNP-oligo-DNAs are illustrated in FIG. 2. In using the SNP-oligo-DNAs of SEQ ID NOS: 2 and 3 having a length of 6 bases, the quenching of the QProbe was not observed in both the perfectly matched and the mismatched sequences (FIG. 2(a)). This is probably because the Tm value of the SNP-oligo-DNA was too low to detect the hybridization of the SNP-oligo-DNA and the QProbe binding DNA under this measurement condition. On the other hand, in using the SNP-oligo-DNAs of SEQ ID NOS: 8 to 11 having a length of 9 to 10 bases, the quenching of the QProbe was observed in both the perfectly matched and the mismatched sequences (FIGS. 2(d) and 2(e)). This is probably because the Tm value of the SNP-oligo-DNA was so high on the contrary that the possibility of the hybridization between the QProbe binding DNA and the SNP-oligo-DNA was not affected by a difference of single base replacement. In using the SNP-oligo-DNAs of SEQ ID NOS: 4 to 7 having a length of 7 or 8 bases, the quenching of the QProbe was observed only in the SNP-oligo-DNA having the perfectly matched sequence (FIGS. 2(b) and 2(c)). It reveals that such a probe can recognize a single base difference. In using this probe, however, the temperature at which the quenching starts in case of the perfect match was as low as 40° C., and hence, there seems to be a possibility that the quenching cannot be observed depending on an experimental environment.

The results obtained by using the linker type SNP-oligo-DNAs are illustrated in FIG. 3. In using a usual oligo DNA having an SNP recognition site of 6 bases or less, the Tm value was too low to hybridize the oligo DNA to the QProbe binding DNA (FIG. 2(a)). On the other hand, in using the linker type SNP-oligo-DNA, even if it had the reporter region of only 4 bases, owing to the anchor region of 15 bases and the linker region of 1 or more bases, the fluorescence quenching was observed without degrading the SNP recognition capability (FIGS. 3(a) to 3(e)).

In order to examine the effect of the linker addition in more detail, the temperature at which the quenching of the QProbe was observed through the hybridization of each SNP-oligo-DNA and the QProbe binding DNA was analyzed. A temperature at which the fluorescence intensity of the QProbe started to lower with the temperature gradually lowered, namely, a temperature at which the slope of each graph of FIGS. 2 and 3 became negative, was defined as the quenching start temperature (illustrated with arrows in FIGS. 2 and 3). These temperatures are summarized in Table 3. In this table, ND means that the quenching was not detected, and Δ° C. stands for a difference between the quenching start temperature obtained in PM and the quenching start temperature obtained in MM.

TABLE 3

| Probe Structure | Number of Bases in SNP Recognition Site | Length of Linker Region | Quenching Start Temperature (° C.) | | Δ° C. (PM − MM) |
|---|---|---|---|---|---|
| | | | PM | MM | |
| SNP-Oligo-DNA | 6 | 0 | ND | ND | — |
| | 7 | 0 | 40.05 | ND | 40.05 |
| | 8 | 0 | 40.05 | ND | 40.05 |
| | 9 | 0 | 40.90 | 32.13 | 8.77 |
| | 10 | 0 | 51.85 | 42.03 | 9.82 |
| Linker type SNP-Oligo DNA | 4 | 1 | 71.67 | 67.70 | 3.97 |
| | 4 | 3 | 67.70 | 47.87 | 19.83 |
| | 4 | 5 | 63.75 | 38.02 | 25.73 |
| | 4 | 7 | 55.72 | ND | 55.72 |
| | 4 | 9 | 45.93 | ND | 45.93 |

In using the SNP-oligo-DNAs, the difference (Δ° C.) in the quenching temperature between the perfect match and the mismatch was maximum when the length was 7 or 8 bases, and the difference value was 40.05° C. On the other hand, in using the linker type SNP-oligo-DNAs, the difference in the quenching temperature was maximum when the linker region had a length of 7 bases, and the difference value was 55.72° C. The quenching started at a higher temperature in the perfect match in using the linker type SNP-oligo-DNAs than in using the SNP-oligo-DNAs. In other words, the linker type SNP-oligo-DNAs were superior in the SNP discrimination capability in a low temperature region than the oligo DNAs having no linker region. This is probably because of high hybridization capability owing to the anchor region.

It was found based on the results of Example 1 that the linker type SNP-oligo-DNAs had high hybridization efficiency and high SNP discrimination capability.

Example 2: Examination on Linker Region

For designing a QProbe binding probe, the sequence of an anchor region and the length of a linker region for hybridizing the probe and a target nucleic acid were examined.

(Materials)

QProbe binding DNA: DNA having a sequence of SEQ ID NO: 22 bound to QProbe.

Linker type SNP-oligo-DNA: Oligo DNA comprising a reporter region consisting of 4 bases and an anchor region consisting of 20 bases, prepared based on DNA having a sequence of SEQ ID NO: 23 or 24 with the lengths of an interval and a linker variously changed. The reporter region corresponded to a sequence of nucleotides 37 to 40 of SEQ ID NO: 23 or 24, and the anchor region corresponded to 20 bases positioned spaced, on the 5' side, from the reporter region by the number of bases corresponding to the interval. Here, the interval refers to the number of bases disposed, in the DNA having the sequence of SEQ ID NO: 23 or 24, between the 5'-end of the reporter region and the 3'-end of the anchor region in designing the reporter region and the anchor region. As the linker, adenine was used.

Hybridization buffer: 50 mM KCl, 10 mM Tris-HCl (pH 8.0), 1.5 mM MgCl$_2$, 0.1% TWEEN-20.

(Method)

The method was performed in the same manner as described in Example 1 except that any of various synthesized DNAs and linker type QProbe binding probes was used.

(Results)

In the results of the Tm analysis performed by using the QProbe binding DNA and various linker type SNP-oligo-DNAs, oligo DNAs causing a large difference in the fluorescence intensity between the perfect match and the mismatch at 25° C. were screened, and these measurement results are summarized in FIG. 4. It was found from these results that when the length of the interval and the length of the linker are larger than 0, the SNP discrimination capability was superior, but too large lengths impair the discrimination capability. In other words, it is shown to be significant to achieve a balance between the length of the interval and the length of the linker without setting merely one of these lengths. In particular, it was revealed that the difference in the fluorescence intensity between the perfect match and the mismatch can be increased and the SNP discrimination capability can be superior by setting the interval to a length of about −3 to +3 as compared with the length of the linker.

Example 3: Hybridization to Synthesized DNA Using Linker Type QProbe Binding Probe The hybridization to various synthesized DNAs was performed by using a linker type QProbe binding probe designed in consideration of the results of Example 2, so as to examine the SNP discrimination capability.

(Materials)

Synthesized DNA: DNA having a sequence of SEQ ID NO: 23, 25, 27 or 29 and perfectly matching with a linker type QProbe binding probe, or DNA having a sequence of SEQ ID NO: 24, 26, 28 or 30 and mismatching with a linker type QProbe binding probe.

Linker type QProbe binding probe: Probe obtained by binding a QProbe to a nucleotide having a sequence of any one of SEQ ID NOS: 31 to 34.

Hybridization buffer: 50 mM KCl, 10 mM Tris-HCl (pH 8.0), 0.1% TWEEN-20.

The characteristics of the linker type QProbe binding probes are shown in Table 4. An underlined portion in each sequence shown in this table corresponds to a base in which an SNP can occur in a synthesized DNA of interest.

TABLE 4

| SEQ ID NO: | Target Gene | Abbreviation | Probe Sequence (5'-3') | Length of Each Region | | | |
|---|---|---|---|---|---|---|---|
| | | | | Reporter | Anchor | Linker | QProbe |
| 31 | N-Acetyl-transferase 2 | NAT-2 | cctg-aaaaaa-aaatcaggagagagcagtat | 4 | 20 | 6 | 5'-Green |
| 32 | GST A1 | GA1-2 | gtgtgggagtggcttttccc-tttttttttt-accc | 4 | 20 | 10 | 3'-Green/Yellow |
| 33 | CYP2C9 | CP-2 | catt-cccc-ctccccaccagcctgcccca | 4 | 20 | 5 | 5'-Green |
| 34 | ALDH2 | AD-2 | tagatggtggctgtaggaat-aaaaaaaaaaaa-gcac | 4 | 20 | 12 | 3'-Green |

(Method)

The method was performed in the same manner as described in Example 1 except that various synthesized DNAs and linker type QProbe binding probes were used.

(Results)

The test results are illustrated in FIG. 5. In using any of the linker type QProbe binding probes, there was a conspicuous difference in the fluorescence intensity between perfect match and mismatch with a corresponding synthesized DNA in the vicinity of 25° C. In particular, in using GST A1 gene, the difference in the fluorescence intensity between the perfect match and the mismatch was large, and the SNP discrimination capability was high. Therefore, it was decided to use the GST A1 gene in an experimental system employed thereafter (FIG. 5(b)).

Example 4: Detection of SNP by LAMP Method

A QProbe binding probe having a short sequence (GST-QP-short), a QProbe binding probe having a long sequence (GST-QP-long) and a QProbe having a linker region (GST-QP-linker) were respectively prepared to measure the SNP discrimination capability for the GST gene by the LAMP method.

(Materials)

Template GST-DNA: DNA having a sequence of SEQ ID NO: 35 (GST-PM) or DNA having a sequence of SEQ ID NO: 36 (GST-MM).

QProbe binding probe: GST-QP-short, GST-QP-long or GST-QP-linker.

LAMP primer: Primer having a sequence of any of SEQ ID NOS: 37 to 40.

LAMP master mix: 50 mM KCl, 20 mM Tricine (pH 8.8), 1.4 mM dNTPs, 8 mM Mg$_2$SO$_4$, 0.1% TWEEN-20, 0.2 µM GST-F3 primer, 0.2 µM GST-B3 primer, 2.4 µM GST-FIP primer, 0.81 µM GST-BIP primer, 16 U Bst pol.

The characteristics of the QProbe binding probes used in Example 4 are shown in Table 5. An underlined portion corresponds to a base where an SNP can occur in a synthesized DNA of interest.

TABLE 5

| SEQ ID NO: | Name of Probe | Target Gene | Probe Sequence (5'-3') | Length of Each Region | | | QProbe |
|---|---|---|---|---|---|---|---|
| | | | | Reporter | Anchor | Linker | |
| 32 | GST-QP-linker | GST A1 | gtgtgggagtggcttttccc-ttttttttttt-ac<u>c</u>c | 4 | 20 | 10 | 3'-Green/Yellow |
| 41 | GST-QP-short | GST A1 | ac<u>c</u>c | 4 | – | – | 3'-Yellow |
| 42 | GST-QP-long | GST A1 | agtggcttttccctaacttgac<u>c</u>c | 24 | – | – | 3'-Yellow |

(Method)

19.75 µL of the LAMP master mix and 0.25 µL of every QProbe binding probe at 10 µM were mixed, and the resultant was dispensed into an 8-tube strip by 20 µL each. To the 8-tube strip, 5.0 µL each of control DNA was added. The template DNA of SEQ ID NO: 35 or 36 was denatured by treating at 95° C. for 5 minutes. The denatured template DNA of SEQ ID NO: 35 or 36 was added to the 8-tube strip to attain $10^5$ cps/test or $10^3$ cps/test. A real-time turbidity measuring apparatus LA-200 (manufactured by Teramecs Co., Ltd.) was used to perform the LAMP method by incubating the 8-tube strip at 65° C. for 1 hour. During the reaction, the turbidity was measured in real time to obtain a Tt value. The Tt value corresponds to a time (in minutes) elapsing until the turbidity of each sample reaches 0.1.

A LAMP product resulting from the amplification reaction was subjected to the Tm analysis using Mx3005P Real-Time PCR System to measure the fluorescence intensity while lowering the temperature from 99° C. to 25° C. The temperature drop rate was set to −2° C./30 seconds.

(Results)

Figure 6:
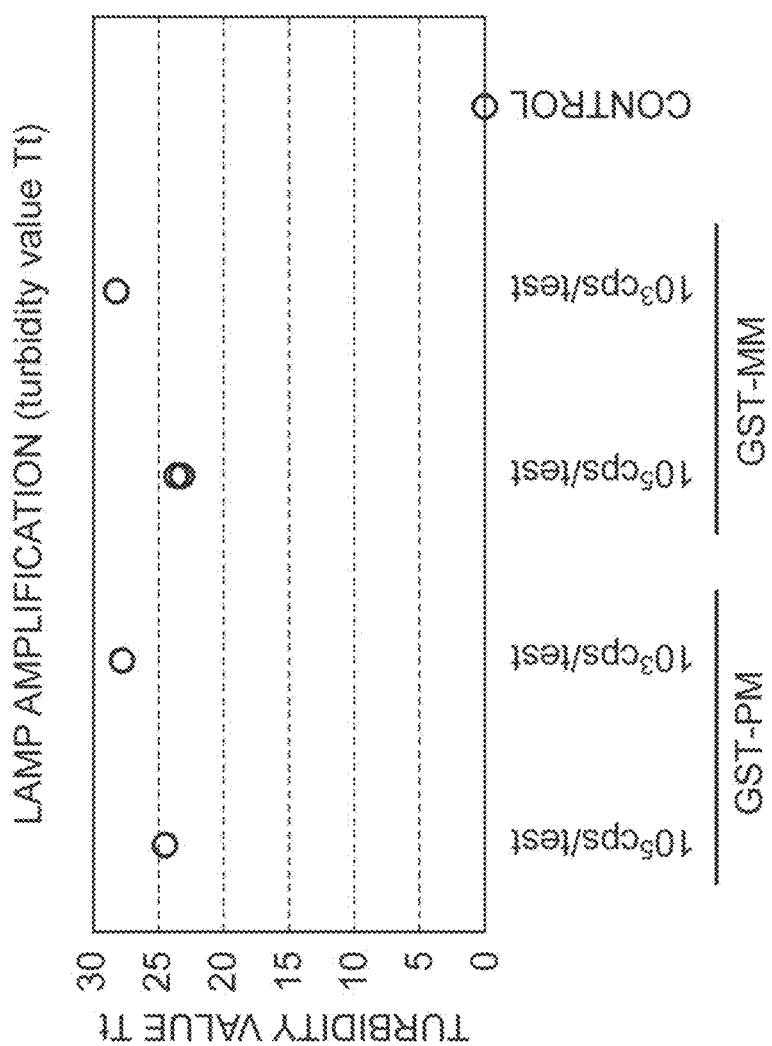
FIG. 6 illustrates amplification efficiency of a template DNA in a LAMP method.

It was confirmed that no difference was caused in the Tt value obtained by the real-time turbidity measurement no matter whether the GST-PM or the GST-MM was used as a template (FIG. 6). Accordingly, it was found that there arises no difference in the amplification efficiency by the LAMP method using the GST-PM and the GST-MM.

Figure 7A:
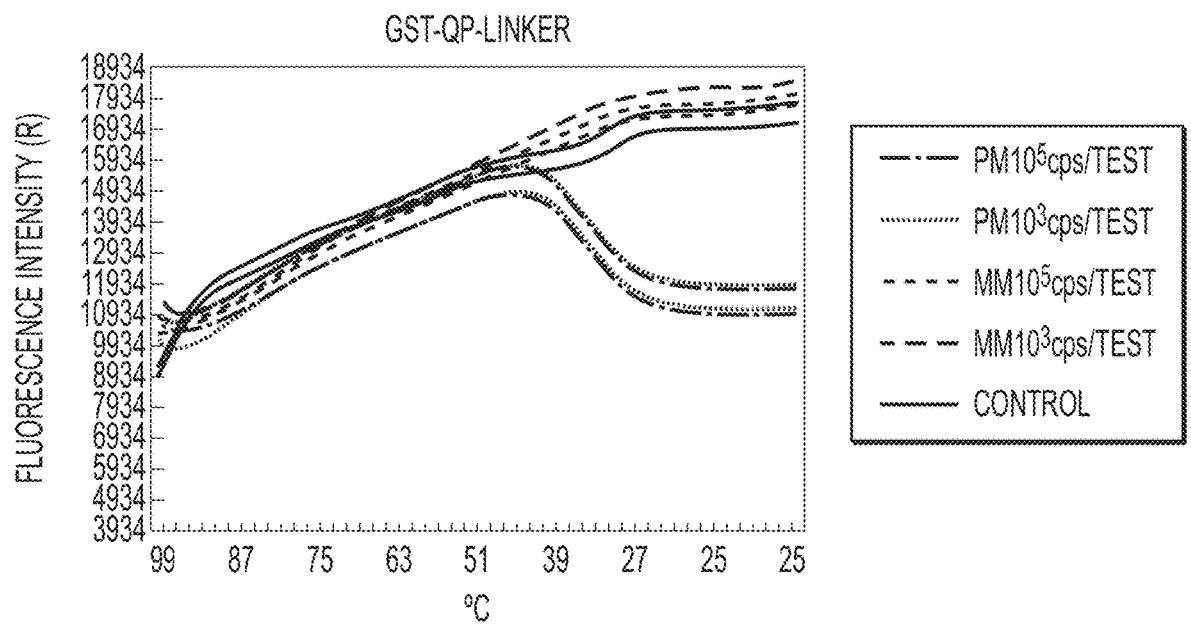
FIG. 7 illustrates results of the Tm analysis obtained by using various GST-QP probes.
Figure 7B:
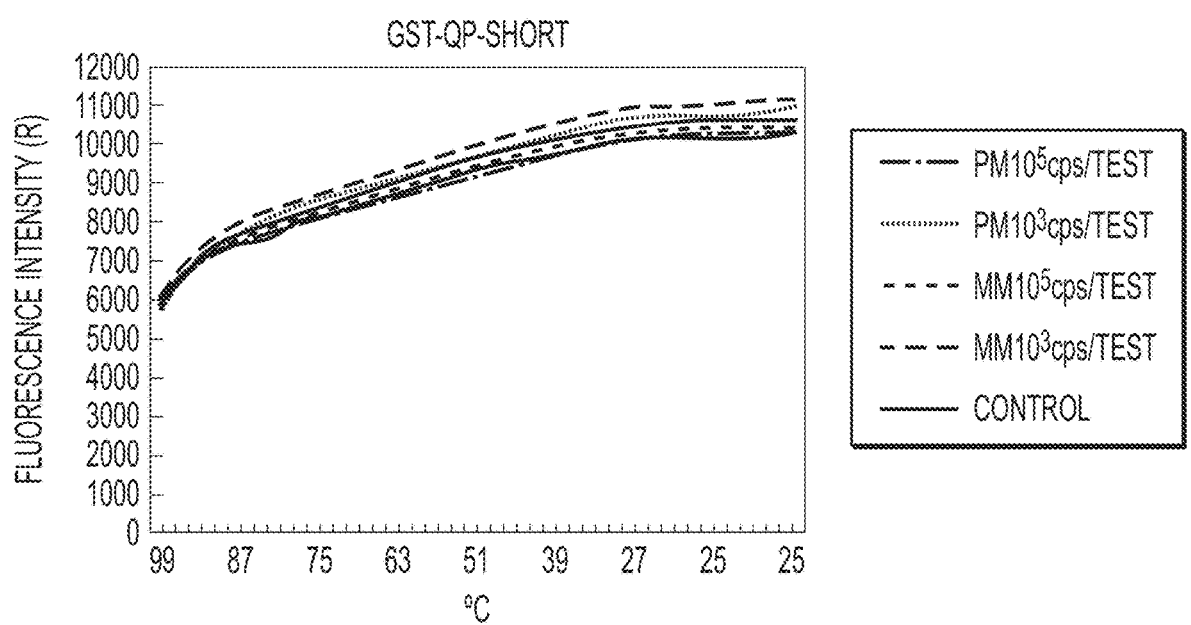
Figure 7C:
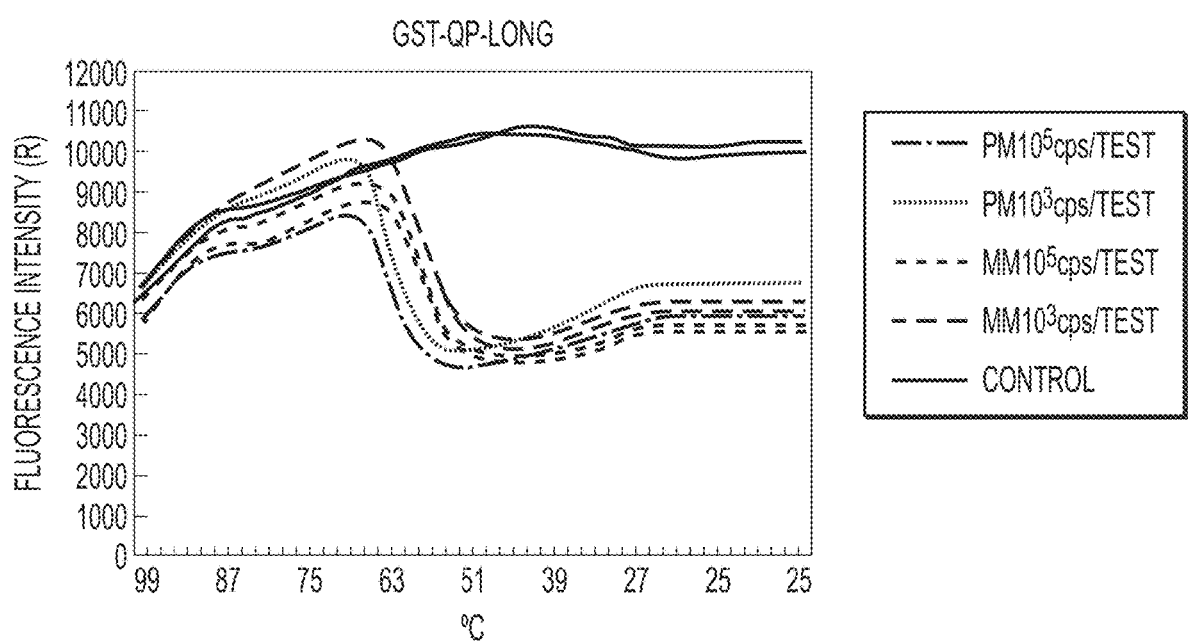

The change of the fluorescence intensity during the Tm analysis is illustrated in FIG. 7. If the GST-QP-short comprising the 4-nucleotide reporter region was used, the hybridization occurred neither to the GST-PM nor to the GST-MM, and the quenching of the QProbe was not observed (FIG. 7(b)). Alternatively, if the GST-QP-long comprising no linker region was used, the hybridization occurred both to the GST-PM and to the GST-MM at substantially the same temperature, and the quenching of the QProbe was observed, and therefore, the SNP analysis was difficult (FIG. 7(c)). On the other hand, if the GST-QP-linker comprising the linker region was used, large quenching was observed in using the GST-PM at either $10^5$ cps/test or $10^3$ cps/test. On the contrary, the fluorescence of the GST-QP-linker was not quenched in using the GST-MM of the mismatched template at all in the same manner as in using the control DNA (FIG. 7(a)). Accordingly, when the QProbe binding probe comprising the linker region was used, an SNP could be specifically detected in the LAMP product, in which the detection was difficult by using the probe comprising no linker region, while retaining the hybridization efficiency for a specific sequence.

Example 5: Detection of SNP by PCR Method

An SNP was detected by the PCR method using a QProbe binding probe comprising a linker region.

(Materials)

Template GST-DNA: DNA having a sequence of SEQ ID NO: 35 (GST-PM) or DNA having a sequence of SEQ ID NO: 36 (GST-MM).

QProbe binding probe: GST-QP-short, GST-QP-long, or GST-QP-linker.

PCR primer: Primer having a sequence of SEQ ID NO: 43 or 44. PCR buffer: 1× Pwo Super yield Buffer, 0.2 mM dNTPs, 1 U Pwo Super yield pol., 0.5× Gelgreen.

(Method)

0.2 µL, of every PCR primer and 14.8 µL of the PCR buffer were mixed, and the resultant was dispensed into an 8-tube strip by 15 µL each. To the resultant 8-tube strip, 5.0 µL each of the control DNA was added. The template DNA of SEQ ID NO: 35 or 36 was added to the 8-tube strip to attain $10^3$ cps/test. A reaction was performed by using Mx3005P Real-Time PCR system under the following conditions: The reaction was performed (1) at 95° C. for 2 minutes, (2) at 95° C. for 15 seconds, (3) at 53° C. for 30 seconds, (4) at 72° C. for 45 seconds, and the processes of (2) to (4) were repeated by 50 cycles. To a PCR product resulting from the reaction, 5.0 µL of every QProbe binding probe in 0.25 µM was added, and the resultant was subjected to the Tm analysis using Mx3005P Real-Time PCR system. The Tm analysis was performed by measuring the fluorescence intensity while lowering the temperature from 99° C. to 25° C. The temperature drop rate was set to −2° C./30 seconds.

(Results)

Figure 8:
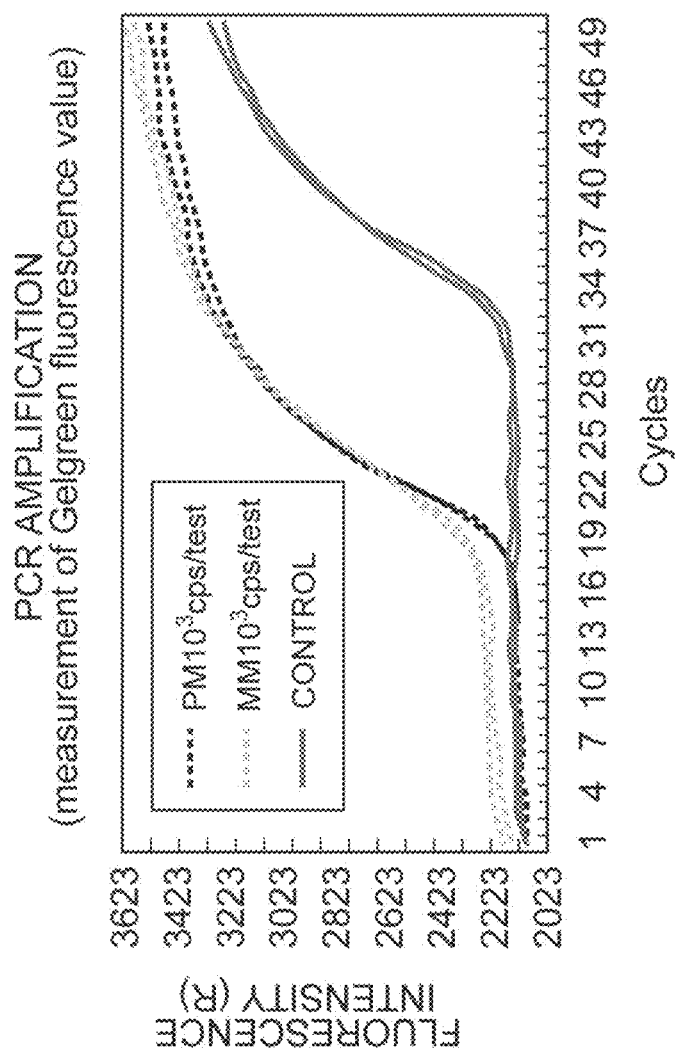
FIG. 8 illustrates amplification efficiency of a template DNA in a PCR method.

A fluorescent intercalator, 0.5× Gelgreen, was used to measure the amplification of the template DNA (FIG. 8). As a result, it was found that there was no difference in the amplification efficiency by the PCR method no matter whether the GST-PM or the GST-MM was used as a template.

Figure 9A:
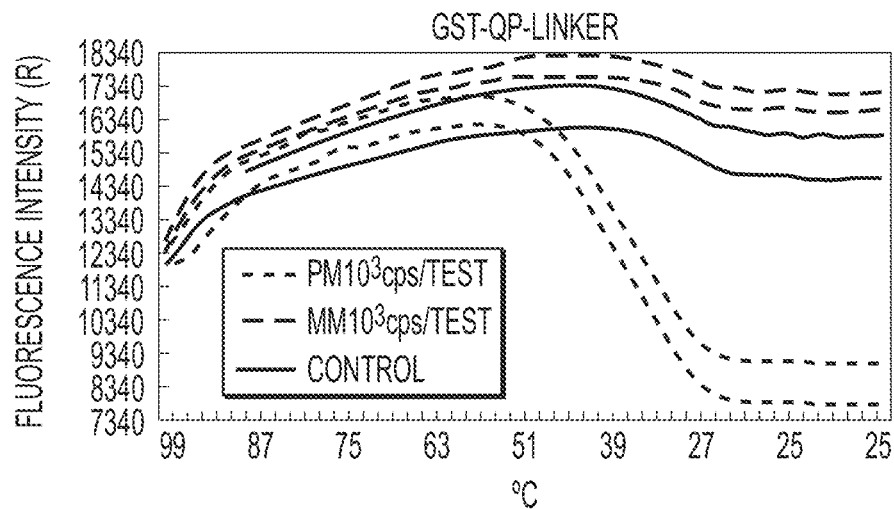
FIG. 9 illustrates results of the Tm analysis obtained by using various GST-QP probes.
Figure 9B:
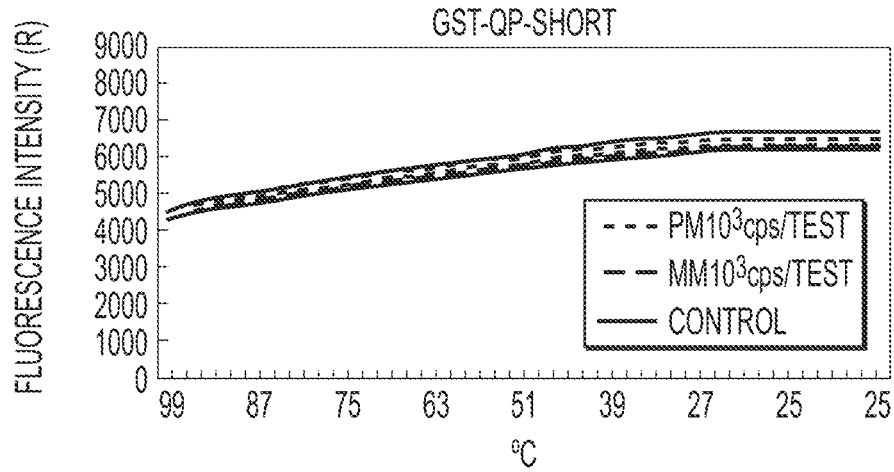
Figure 9C:
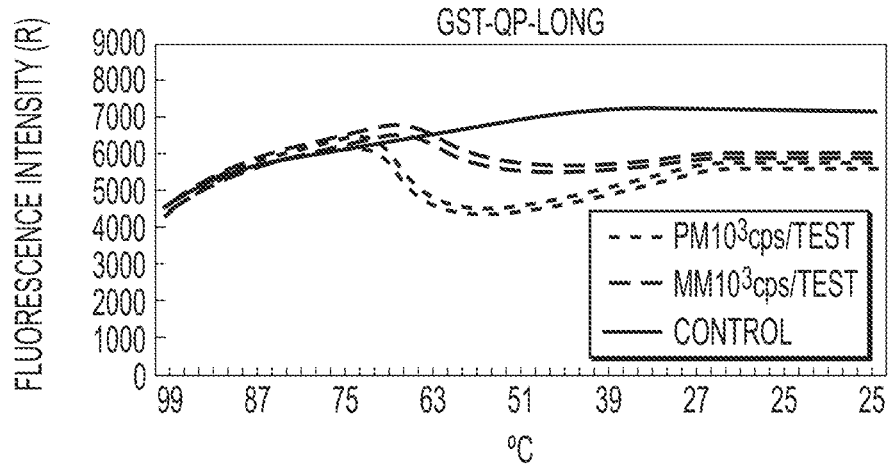

The change of the fluorescence intensity during the Tm analysis is illustrated in FIG. 9. In the same manner as in Example 4, if the GST-QP-short was used, the hybridization occurred neither to the GST-PM nor to the GST-MM, and the quenching of the QProbe was not observed (FIG. 9(b)). If the GST-QP-long comprising no linker region was used, although the fluorescence intensity was different in the vicinity of the quenching start temperature, there was substantially no difference around room temperature. Besides, the GST-QP-long hybridized both to the GST-PM and to the GST-MM at substantially the same temperature, and the quenching of the QProbe was observed (FIG. 9(c)). If the GST-QP-linker comprising the linker region was used, large quenching was observed in using the GST-PM. On the contrary, in using the GST-QP-linker, the fluorescence was not quenched in using the GST-MM of the mismatched template in the same manner as in using the control DNA (FIG. 9(a)). Accordingly, when the QProbe binding probe comprising the linker region was used, an SNP could be specifically detected not only by the LAMP method but also by the PCR method.

The invention claimed is:

1. A probe for single nucleotide polymorphism detection to be used for a target nucleic acid sequence where a single nucleotide polymorphism is present, wherein
the target nucleic acid sequence comprises a first target sequence corresponding to a region comprising the single nucleotide polymorphism, and a second target sequence positioned on a 3' or 5' side of the first target sequence and corresponding to a region without the single nucleotide polymorphism,
the probe comprises a reporter region for detecting the single nucleotide polymorphism, an anchor region, and a linker region,
the reporter region comprises nucleotides consisting of a sequence perfectly matching with the first target sequence when a nucleotide of the single nucleotide polymorphism is a first nucleotide, and mismatching with the first target sequence when the nucleotide is a nucleotide other than the first nucleotide; and a fluorescent dye quenching when the first target sequence and the reporter region hybridize,
the anchor region comprises nucleotides consisting of a sequence complementary to the second target sequence, and
the linker region links the reporter region and the anchor region to each other, comprises nucleotides consisting of a sequence non-complementary to a sequence between the first target sequence and the second target sequence in the target nucleic acid sequence, and
the linker region consists of a sequence not comprising a universal base.

2. The probe according to claim 1, wherein the linker region consists of only one kind of base selected from adenine, guanine, cytosine and thymine.

3. The probe according to claim 2, wherein the linker region consists of 3 to 11 nucleotides.

4. The probe according to claim 1, wherein the linker region consists of 3 to 11 nucleotides.

5. The probe according to claim 1, wherein the fluorescent dye is selected from the group consisting of FITC, TMR, 6-joe, Bodipy-FL/C6 and Bodipy-FL/C3.

6. The probe according to claim 1, wherein the fluorescent dye quenches when cytosine in the reporter region hybridizes to guanine in the target nucleic acid sequence.

7. The probe according to claim 1, wherein the target nucleic acid sequence is a human nucleic acid sequence.

8. A method of detecting a single nucleotide polymorphism in a target nucleic acid sequence, comprising:
preparing a mixture by mixing a probe and a target nucleic acid sequence comprising a single nucleotide polymorphism;
measuring fluorescence intensity of the mixture; and
detecting the presence/absence of the single nucleotide polymorphism in the target nucleic acid sequence on the basis of the fluorescence intensity,
wherein the target nucleic acid sequence comprises a first target sequence corresponding to a region comprising the single nucleotide polymorphism, and a second target sequence positioned on a 3' or 5' side of the first target sequence and corresponding to a region without the single nucleotide polymorphism,
the probe comprises a reporter region for detecting the single nucleotide polymorphism, an anchor region, and a linker region,
the reporter region comprises nucleotides consisting of a sequence perfectly matching with the first target sequence when a nucleotide of the single nucleotide polymorphism is a first nucleotide, and mismatching with the first target sequence when the nucleotide is a nucleotide other than the first nucleotide; and a fluorescent dye quenching when the first target sequence and the reporter region hybridize,
the anchor region comprises nucleotides consisting of a sequence complementary to the second target sequence,
the linker region links the reporter region and the anchor region to each other, and comprises nucleotides consisting of a sequence non-complementary to a sequence between the first target sequence and the second target sequence in the target nucleic acid sequence, and
the linker region is an oligonucleotide consisting of a sequence not comprising a universal base.

9. The method according to claim 8, wherein the linker region is an oligonucleotide consisting of only one kind of base selected from adenine, guanine, cytosine and thymine.

10. The method according to claim 8, wherein the linker region is an oligonucleotide consisting of 3 to 11 nucleotides.

11. The method according to claim 8, wherein the fluorescent dye is selected from the group consisting of FITC, TMR, 6-joe, Bodipy-FL/C6 and Bodipy-FL/C3.

12. A method of detecting a single nucleotide polymorphism in a target nucleic acid sequence, comprising:
preparing a mixture by hybridizing:
(i) a reporter region of a probe to a first target sequence of the target nucleic acid sequence,
wherein the reporter region of the probe comprises a fluorescent dye quenching when the first target sequence and the reporter region hybridize, and
the first target sequence comprises a single nucleotide polymorphism, and (ii) an anchor region of the probe to a second target sequence of the target nucleic acid sequence,
wherein the second target sequence is positioned on a 3' or 5' side of the first target sequence and does not include the single nucleotide polymorphism;
   measuring fluorescence intensity of the mixture; and
   detecting the presence/absence of the single nucleotide polymorphism in the target nucleic acid sequence on the basis of the fluorescence intensity,
   wherein the probe comprises the reporter region, the anchor region, and a linker region linking the reporter region and the anchor region and comprising a sequence non-complementary to a sequence between the first target sequence and the second target sequence in the target nucleic acid sequence,
a length of the nucleotides of the reporter region is shorter than a length of the nucleotides of the anchor region, and
the linker region consists of 3 to 11 nucleotides having only one kind of base selected from adenine, guanine, cytosine and thymine.

13. The method of claim 12, wherein
the fluorescent dye is selected from the group consisting of FITC, TMR, 6-joe, Bodipy-FL/C6 and Bodipy-FL/C3, and
the target nucleic acid sequence is a human nucleic acid sequence.

* * * * *